US012320736B2

United States Patent
Mieras et al.

(10) Patent No.: US 12,320,736 B2
(45) Date of Patent: Jun. 3, 2025

(54) SELF-CONTAINED CONDUCTIVITY CONCENTRATION PROFILING SYSTEM

(71) Applicant: The Government of the United States of America, as represented by the Secretary of the Navy, Arlington, VA (US)

(72) Inventors: Ryan S. Mieras, Wilmington, NC (US); Jack A. Puleo, Newark, DE (US); Charles Key, Diamondhead, MS (US); Edward F. Braithwaite, Covington, LA (US); Joseph Calantoni, Diamondhead, MS (US)

(73) Assignee: The Government of the United States of America, as represented by the Secretary of the Navy, Arlington, VA (US)

( * ) Notice: Subject to any disclaimer, the term of this patent is extended or adjusted under 35 U.S.C. 154(b) by 0 days.

(21) Appl. No.: 17/211,529

(22) Filed: Mar. 24, 2021

(65) Prior Publication Data

US 2021/0302297 A1    Sep. 30, 2021

Related U.S. Application Data

(60) Provisional application No. 62/993,828, filed on Mar. 24, 2020.

(51) Int. Cl.
*G01N 15/06*   (2024.01)
(52) U.S. Cl.
CPC .............................. *G01N 15/0656* (2013.01)
(58) Field of Classification Search
CPC ............... G01N 15/06; G01N 15/0656; G01N 2015/1254; G01N 2015/1263;
(Continued)

(56) References Cited

U.S. PATENT DOCUMENTS

| 9,863,622 | B1 * | 1/2018 | Armer ................ F21V 23/0414 |
| 10,180,360 | B1 * | 1/2019 | Naranjo ................ G01K 1/026 |

(Continued)

FOREIGN PATENT DOCUMENTS

WO    2019/023506 A1    1/2019

OTHER PUBLICATIONS

Written Opinion in corresponding PCT/US2021/024018, mailed Jul. 13, 2021, 5 pages.

(Continued)

*Primary Examiner* — Son T Le
*Assistant Examiner* — Matthew W. Baca
(74) *Attorney, Agent, or Firm* — US Naval Research Laboratory; Nigel R. Fontenot

(57) ABSTRACT

Systems and methods are provided for developing a self-contained conductivity concentration profiler (CCP) system for standalone coastal and ocean deployment. A self-contained CCP system in accordance with an embodiment of the present disclosure can measure sediment concentration profiles and track instantaneous bed levels in sandy environments to enable better understanding of small-scale sediment transport processes in the coastal and nearshore marine environment. A self-contained CCP system in accordance with an embodiment of the present disclosure can support unmanned and standalone deployment configuration, allowing for operation in previously unattainable areas of interest in which small-scale sediment transport processes are important but poorly understood.

7 Claims, 30 Drawing Sheets

(58) Field of Classification Search
CPC ... G01N 2015/0042; G01N 2015/0053; G01N 33/18; G01N 33/1886
See application file for complete search history.

(56) References Cited

U.S. PATENT DOCUMENTS

| | | | |
|---|---|---|---|
| 2012/0145561 A1* | 6/2012 | Coulon | G01N 33/1886 205/778.5 |
| 2014/0224167 A1 | 8/2014 | Gasparoni et al. | |
| 2014/0355645 A1 | 12/2014 | Cheng et al. | |
| 2018/0010733 A1* | 1/2018 | Shepherd | F16B 2/185 |
| 2018/0292208 A1* | 10/2018 | Moore | G01N 33/1886 |
| 2020/0011768 A1* | 1/2020 | Dong | F04B 23/02 |

OTHER PUBLICATIONS

International Search Report in corresponding PCT/US2021/024018, mailed Jul. 13, 2021, 4 pages.

Lanckriet, T., Puleo, J. A., & Waite, N. (2013). A Conductivity Concentration Profiler for Sheet Flow Sediment Transport. IEEE Journal of Oceanic Engineering, 38(1), 55-70.

Puleo, J. A., Faries, J., Davidson, M., & Hicks, B. (2010). A Conductivity Sensor for Nearbed Sediment Concentration Profiling. Journal of Atmospheric and Oceanic Technology, 27(2), 397-408.

Van der Zanden, J., Alsina, J. M., Caceres, I., Buijsrogge, R. H., & Ribberink, J. S. (2015). Bedlevel motions and sheet flow processes In the swash zone: Observations with a new conductivity-based concentration measuring technique (CCM+l, Coastal Eng., 105, 47-65.

Ribberink, J. S., & Al-Salem, A. A. (1995). Sheet flow and suspension of sand in oscillatory boundary layers. Coastal Eng., 25(3-4), 205-225.

Horikawa, K., Watanabe, A., & Katorl, s. (1982). Sediment Transport Under Sheet Flow Condition. Coastal Engineering Proc., 1(18).

* cited by examiner

302

308

106

SELF-CONTAINED CONDUCTIVITY CONCENTRATION PROFILING SYSTEM

CROSS REFERENCE TO RELATED APPLICATIONS

This application claims the benefit of U.S. Provisional Patent Application No. 62/993,828, filed on Mar. 24, 2020, which is incorporated by reference herein in its entirety.

FEDERALLY SPONSORED RESEARCH AND DEVELOPMENT

The United States Government has ownership rights in this invention. Licensing inquiries may be directed to Office of Technology Transfer at US Naval Research Laboratory, Code 1004, Washington, DC 20375, USA; +1.202.767.7230; techtran@nrl.navy.mil, referencing Navy Case Number 112045-US2.

FIELD OF THE DISCLOSURE

This disclosure relates to water analysis systems, including water conductivity analysis systems.

BACKGROUND

Conductivity concentration profiler (CCP) systems can be used to determine the conductivity of a fluid-sediment mixture in coastal environments, such as water. In prior CCP systems, power, communications, and instrument control are carried out via cable-to-shore, requiring human interaction and severely limiting the locations and applications for deployment to within 100 m of the control trailer. The control trailer also requires power input in prior CCP systems, further limiting possible deployment locations.

Prior CCP systems have several disadvantages, such as mud sticking to the probe tip, which fouls measurements. Even if the probes in prior CCP systems are in "clear water," they can give an extremely high concentration reading. Further, sampling probes in prior CCP systems are fragile, resulting in probe failures and data loss. Additionally, prior CCP systems have no internal logging, which limits deployment location and deployment conditions. Prior systems have great difficulty deploying in remote locations, or during storm events, where cables and land-based trailers are completely impractical. Some prior CCP systems involve a face seal around the probe and a threaded seal with the instrument housing, and this face seal can be easily compromised by even a single grain of sand, resulting in water intrusion and destruction of the internal circuitry. Also, prior systems using a threaded seal capture method often failed due to poor seals, resulting in water intrusion.

BRIEF DESCRIPTION OF THE DRAWINGS/FIGURES

The accompanying drawings, which are incorporated in and constitute part of the specification, illustrate embodiments of the disclosure and, together with the general description given above and the detailed descriptions of embodiments given below, serve to explain the principles of the present disclosure. In the drawings.

Figure 1:
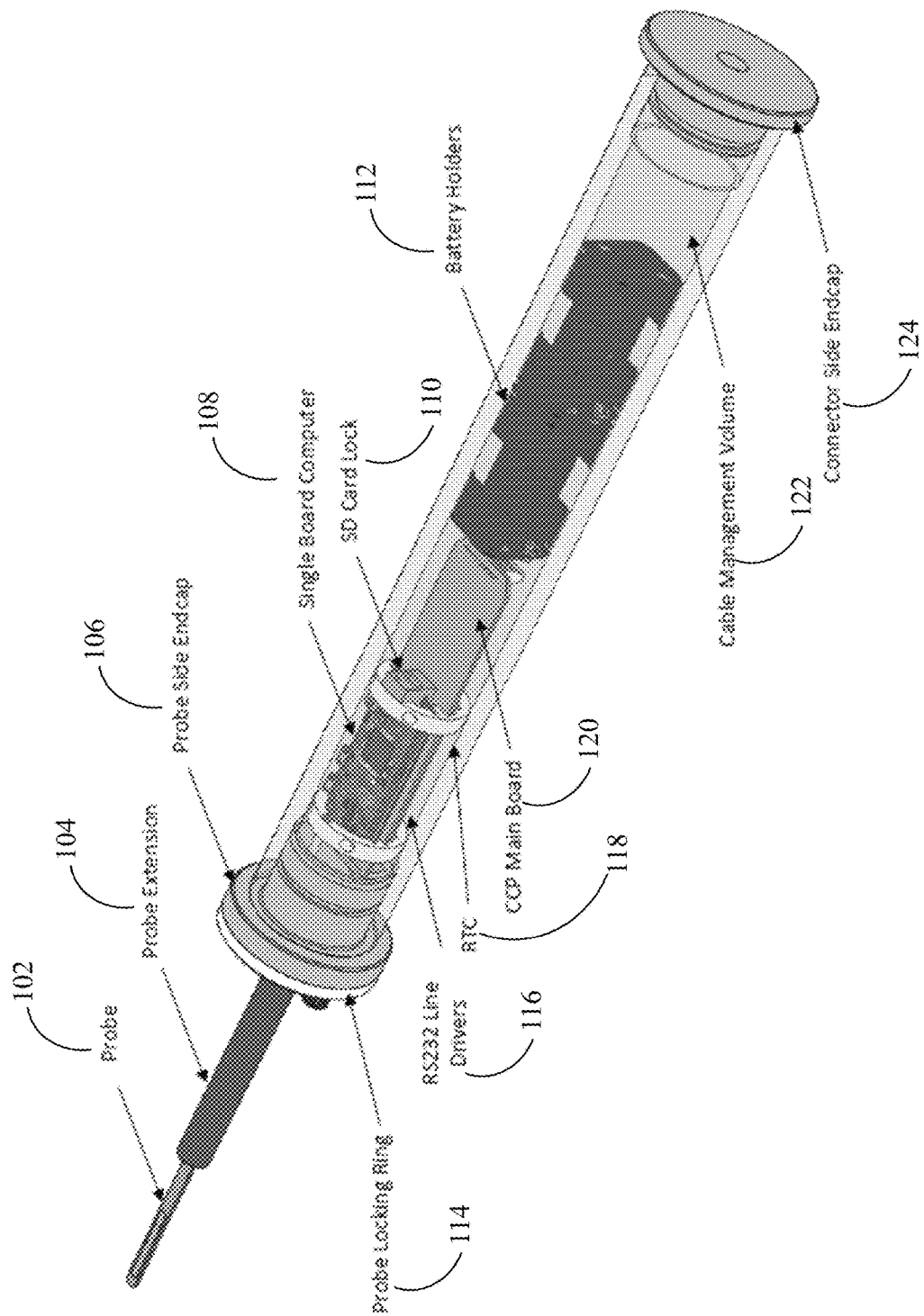
FIG. 1 is a diagram of an exemplary self-contained CCP system in accordance with an embodiment of the present disclosure.

Features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

In the following description, numerous specific details are set forth to provide a thorough understanding of the disclosure. However, it will be apparent to those skilled in the art that the disclosure, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring aspects of the disclosure.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to understand that such description(s) can affect such feature, structure, or characteristic in connection with other embodiments whether or not explicitly described.

1. Overview

Embodiments of the present disclosure provide systems and methods for developing a self-contained conductivity concentration profiler (CCP) system for standalone coastal and ocean deployment. A CCP system in accordance with an embodiment of the present disclosure can measure sediment concentration profiles and track instantaneous bed levels in sandy environments to enable better understanding of small-scale sediment transport processes in the coastal and near-shore marine environment. A CCP system in accordance with an embodiment of the present disclosure can support unmanned and standalone deployment configuration, allowing for operation in previously unattainable areas of interest in which small-scale sediment transport processes are important but poorly understood.

2. Systems

CCP systems in accordance with embodiments of the present disclosure have improved mechanical designs, provide integrated electrical systems, have a rapid-deployment mechanism, and enable autonomous data logging.

2.1. Mechanical Design of Exemplary CCP Systems

FIG. 1 is a diagram of an exemplary self-contained CCP system in accordance with an embodiment of the present disclosure. The CCP system of FIG. 1 has improved CCP electronics and housing and enables self-logging, as well as improved architecture for higher resolution measurements. The CCP system of FIG. 1 includes a probe 102, a probe extension 104 (e.g., in an embodiment, a probe stiffener extension), a probe side endcap 106, a probe locking ring 114, a probe side endcap 106, a single board computer 108 (e.g., in an embodiment, a raspberry pi zero single board computer), drivers 116 (e.g., Recommended Standard (RS) 232 line drivers), a real-time clock (RTC) 118, a CCP main board 120, an SD card lock 110, battery holder 112 (e.g., a 4×4 AA cell battery holder in an embodiment), cable management volume 122, and a connector side endcap 124. In an embodiment, single board computer 108 receives data measured by the CCP system of FIG. 1 and stores it for later use (e.g., on a MicroSD card used with SD card lock 110). In an embodiment, the CCP system of FIG. 1 is configured to measure data either continuously or in bursts based on mission parameters, and RTC 118 controls the timing of the bursts. In an embodiment, measuring data in bursts in this way extends the life of the CCP system.

Figure 2:
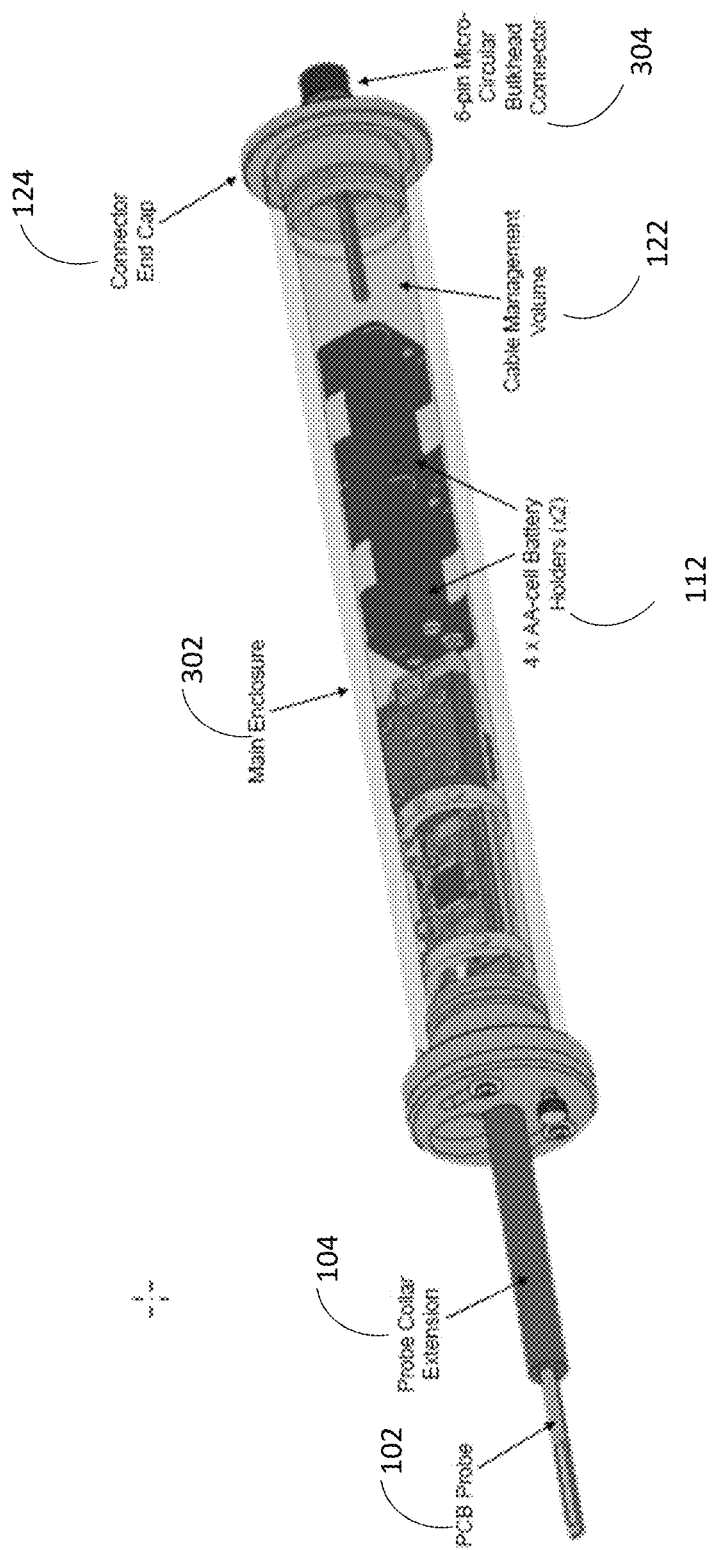
FIG. 2 is another diagram of an exemplary CCP system in accordance with an embodiment of the present disclosure.

FIG. 2 is another diagram of an exemplary CCP system in accordance with an embodiment of the present disclosure. FIG. 2 shows the main enclosure 302 of the CCP system and a bulkhead connector 304 (e.g., a 6-pin micro-circular bulkhead connector).

Figure 3:
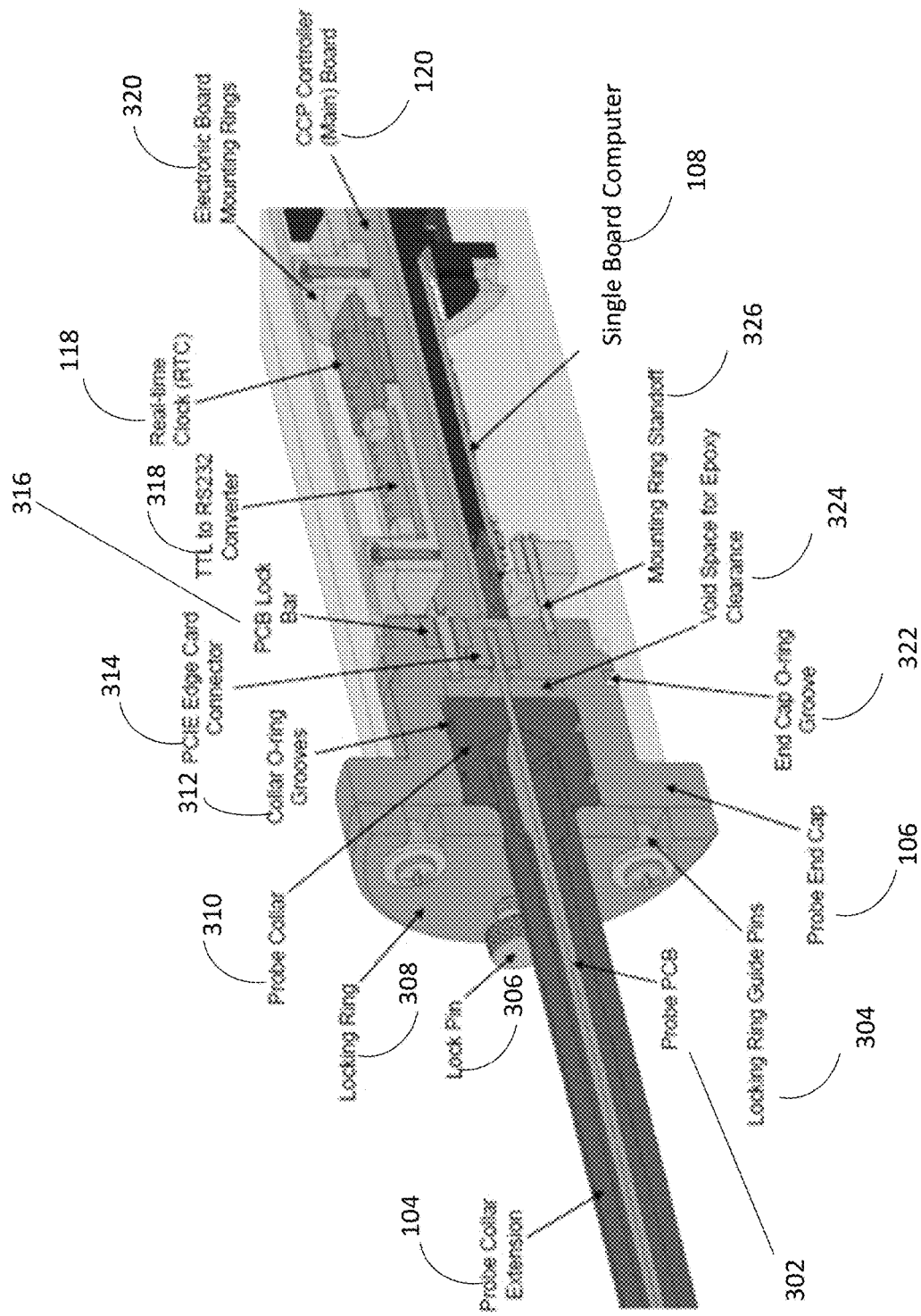
FIG. 3 is a diagram showing exemplary internal components of a CCP system in accordance with an embodiment of the present disclosure.

FIG. 3 is a diagram showing exemplary internal components of a CCP system in accordance with an embodiment of the present disclosure. FIG. 3 shows a probe PCB 302 of probe 102, a locking ring guiding pin 304, a lock pin 306, a locking ring 308, a probe collar 310, probe collar O-ring grooves 312, a PCI Express (PCIE) edge card connector 314, PCB lock bar 316, TTL to RS232 converter 318, electronic board mounting rings 320, end cap O-ring groove 322, void space for epoxy clearance 324, and mounting ring standoff 326.

Figure 4:
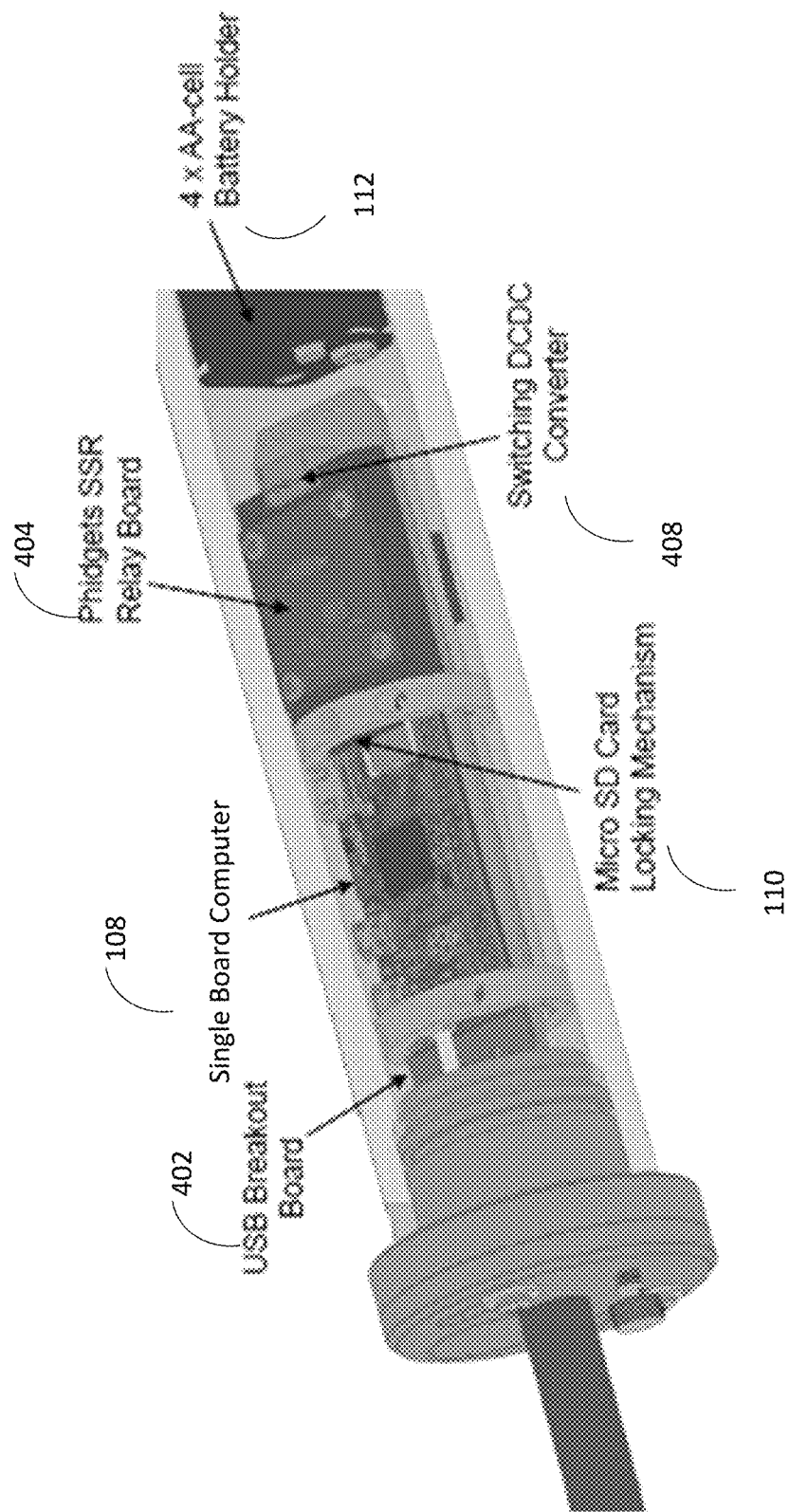
FIG. 4 is another diagram showing exemplary internal components of a CCP system in accordance with an embodiment of the present disclosure.

FIG. 4 is another diagram showing exemplary internal components of a CCP system in accordance with an embodiment of the present disclosure. FIG. 4 shows a Universal Serial Bus (USB) breakout board 402, a relay board (e.g., a Phidgets SSR relay board) 404, and switching direct current (DC) to DC converter 408.

Figure 5:
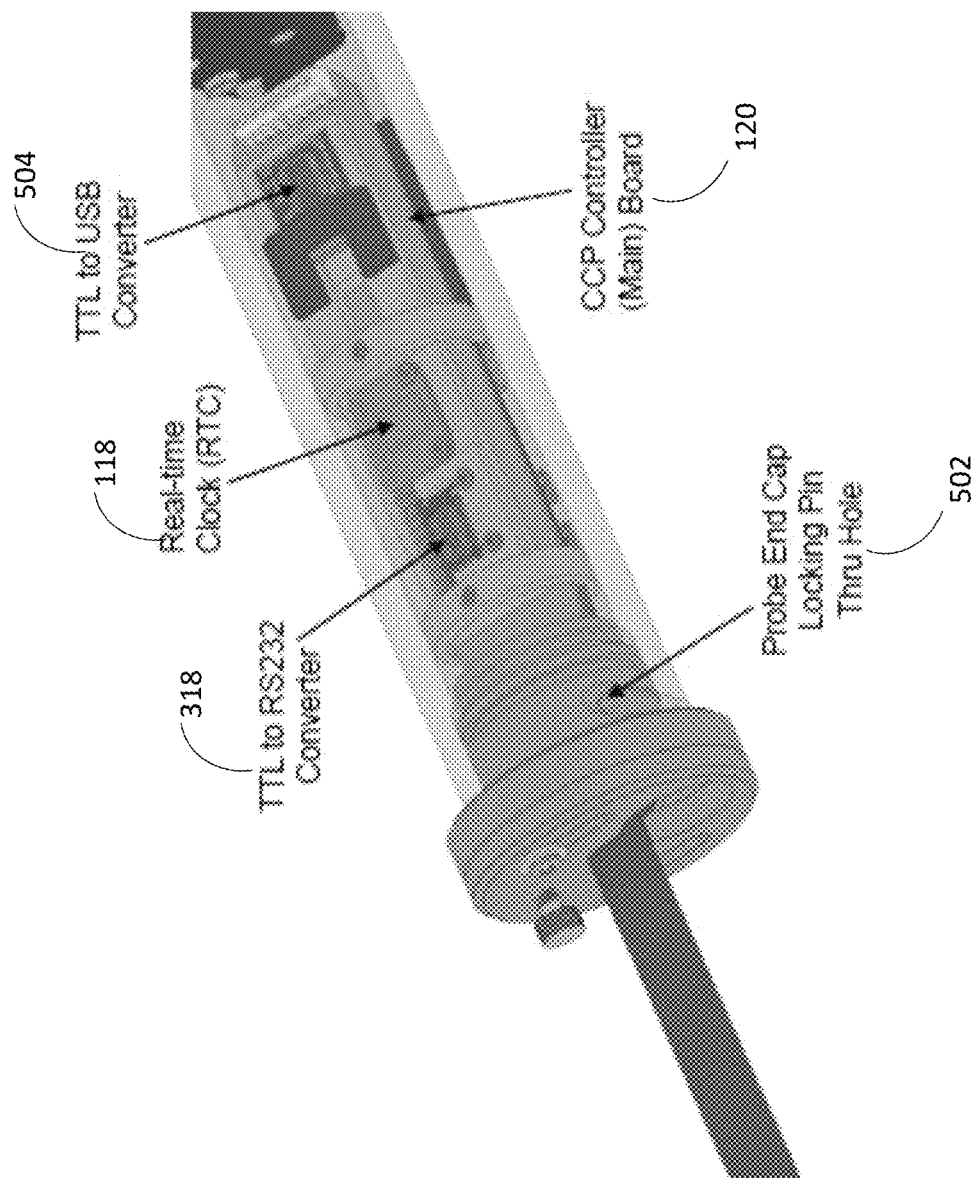
FIG. 5 is another diagram showing exemplary internal components of a CCP system in accordance with an embodiment of the present disclosure.

FIG. 5 is another diagram showing exemplary internal components of a CCP system in accordance with an embodiment of the present disclosure. FIG. 5 shows a probe end cap locking pin thru hole 502 and a TTL to USB converter 504.

Figure 6:
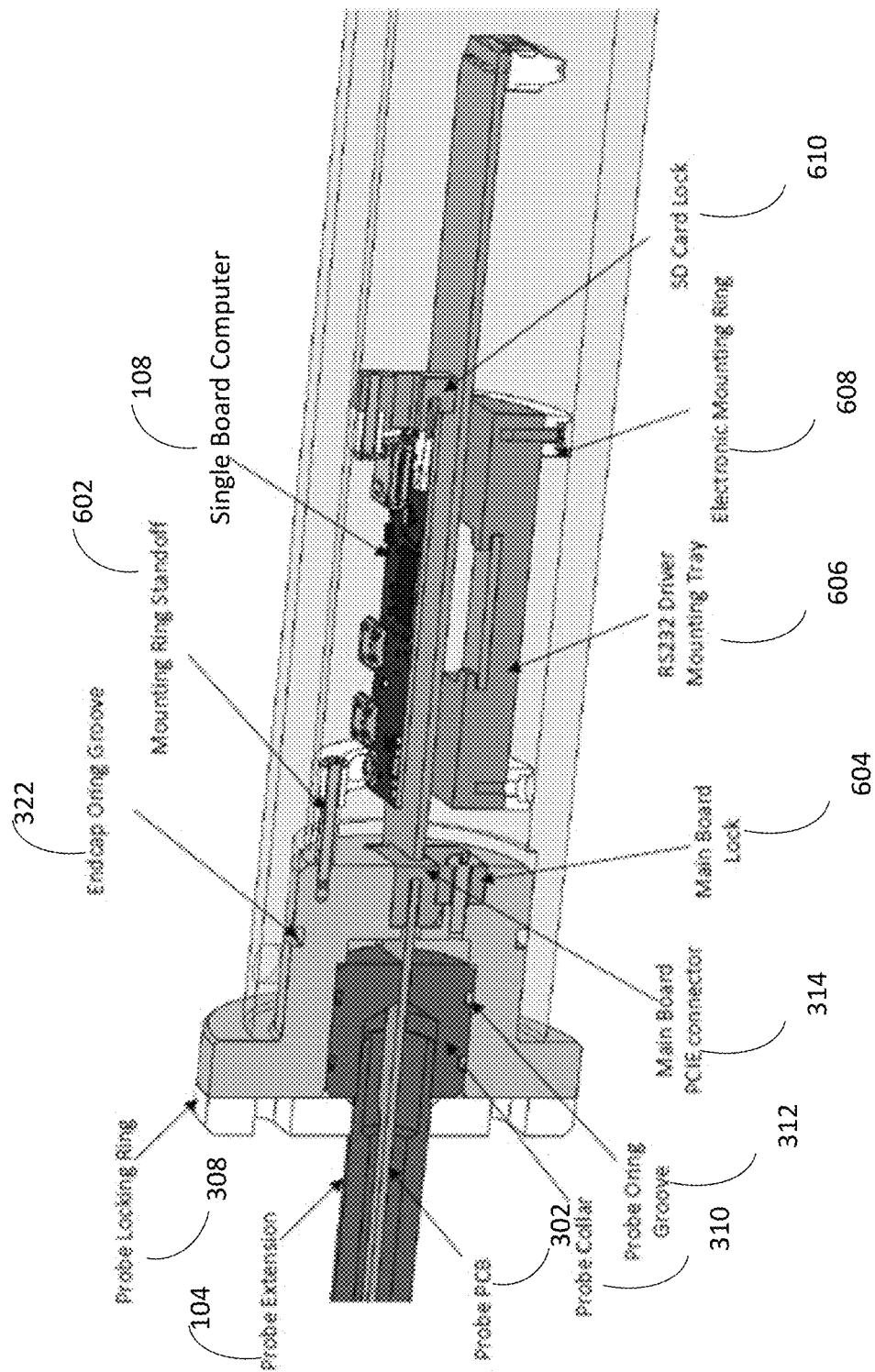
FIG. 6 is another diagram showing exemplary internal components of a CCP system in accordance with an embodiment of the present disclosure.

FIG. 6 is another diagram showing exemplary internal components of a CCP system in accordance with an embodiment of the present disclosure. FIG. 6 shows a mounting ring standoff 602, a main board lock 604, a RS232 driver mounting tray 606, an electronic mounting ring 608, and an SD card lock 610.

Figure 7:
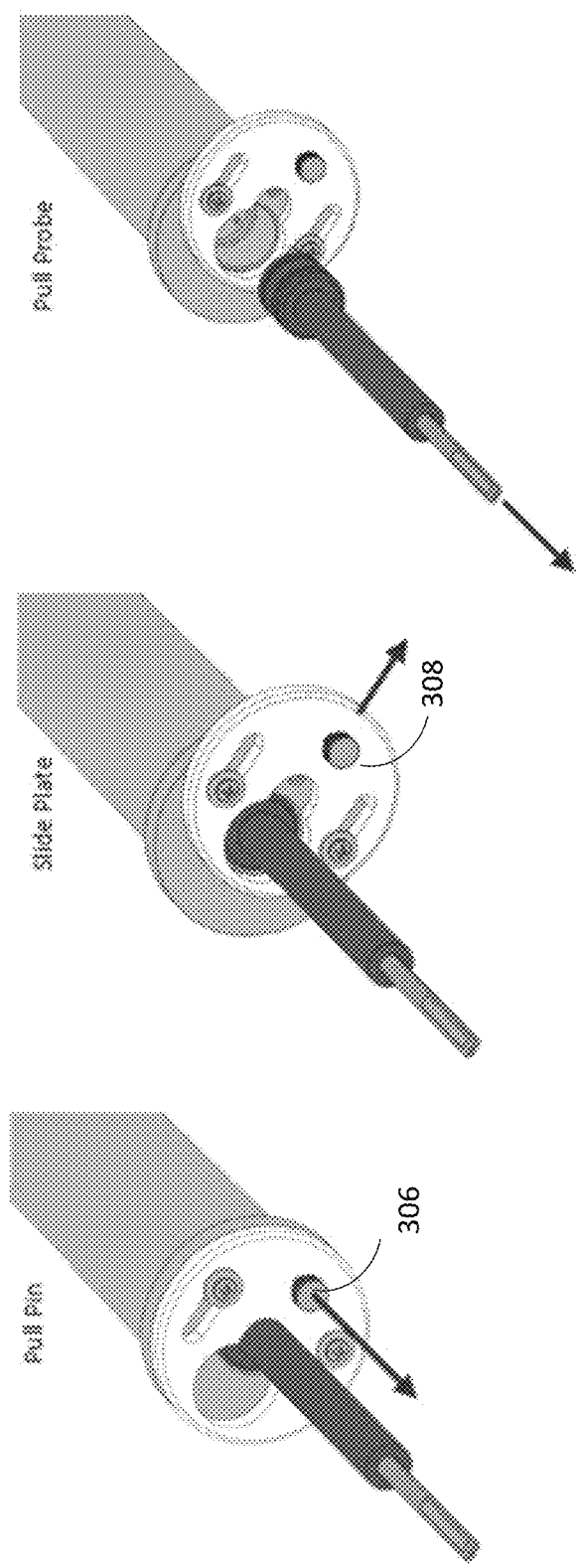
FIG. 7 is a diagram showing the slide plate of a CCP system in accordance with an embodiment of the present disclosure.

FIG. 7 is a diagram showing the slide plate of a CCP system in accordance with an embodiment of the present disclosure. In FIG. 7, lock pin 206 can be removed to enable locking ring 308 to slide and release the probe assembly.

Figure 8:
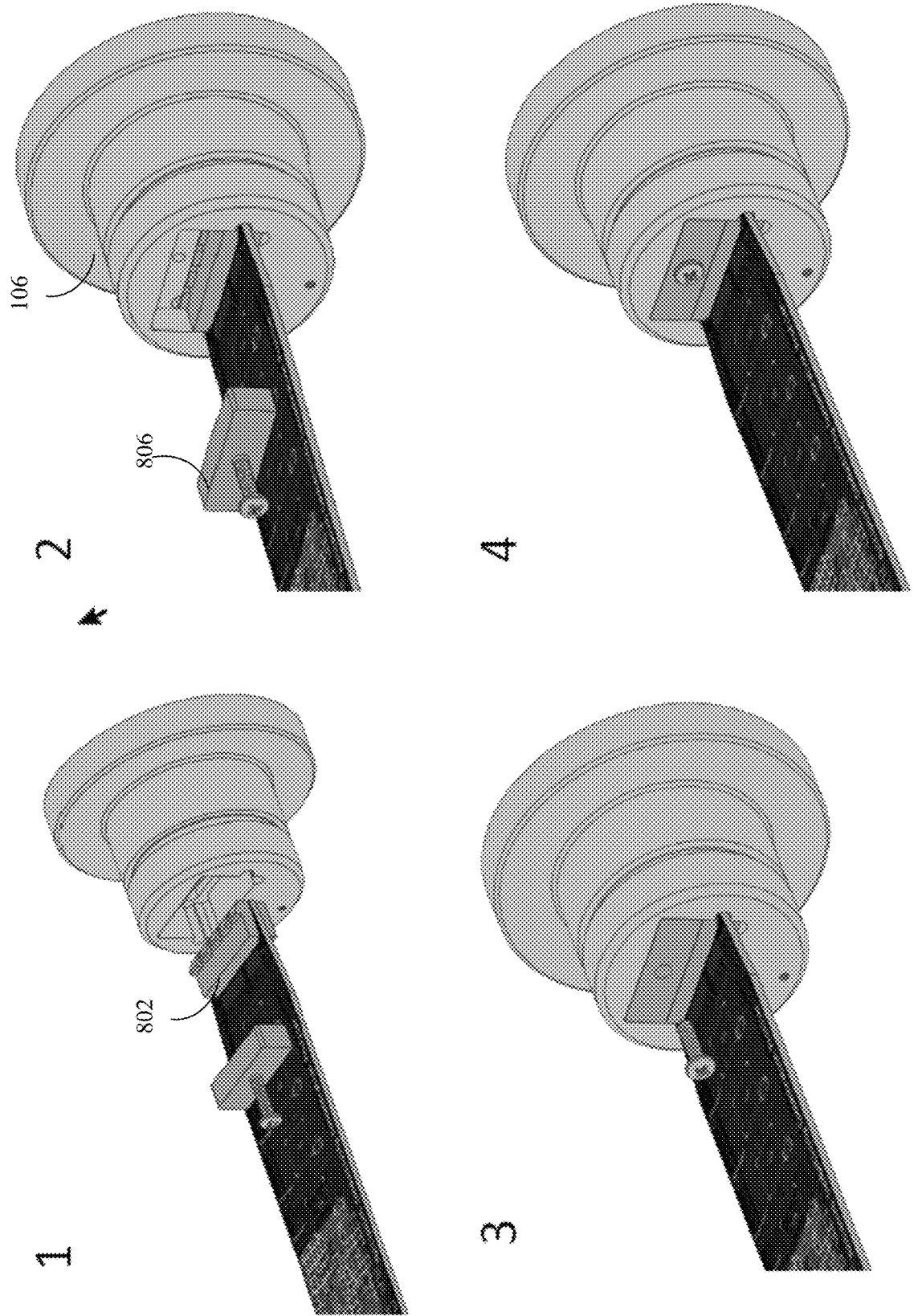
FIG. 8 is a diagram illustrating securing a printed circuit board (PCB) to a probe end cap of an exemplary CCP system with a PCB lock bar in accordance with an embodiment of the present disclosure.

FIG. 8 is a diagram illustrating securing a printed circuit board (PCB) to a probe end cap of an exemplary CCP system with a PCB lock bar in accordance with an embodiment of the present disclosure. In FIG. 8, an asymmetric PCI express edge card connector 802 of the PCB is inserted into a probe end cap 106, and a PCB lock bar 806 is attached to probe end cap 106 and screwed in place to secure the PCB into probe end cap 106. In an embodiment, the probe end cap 106 and PCB mounting mechanism of FIG. 8 enables more secure mounting and reduces the quantity of poor data quality due to a loose connection. Further, in an embodiment, probe end cap 106 reduces the water intrusion risk, increasing the range of deployment conditions (e.g., deeper water, large wave storm conditions, etc.).

Figure 9:
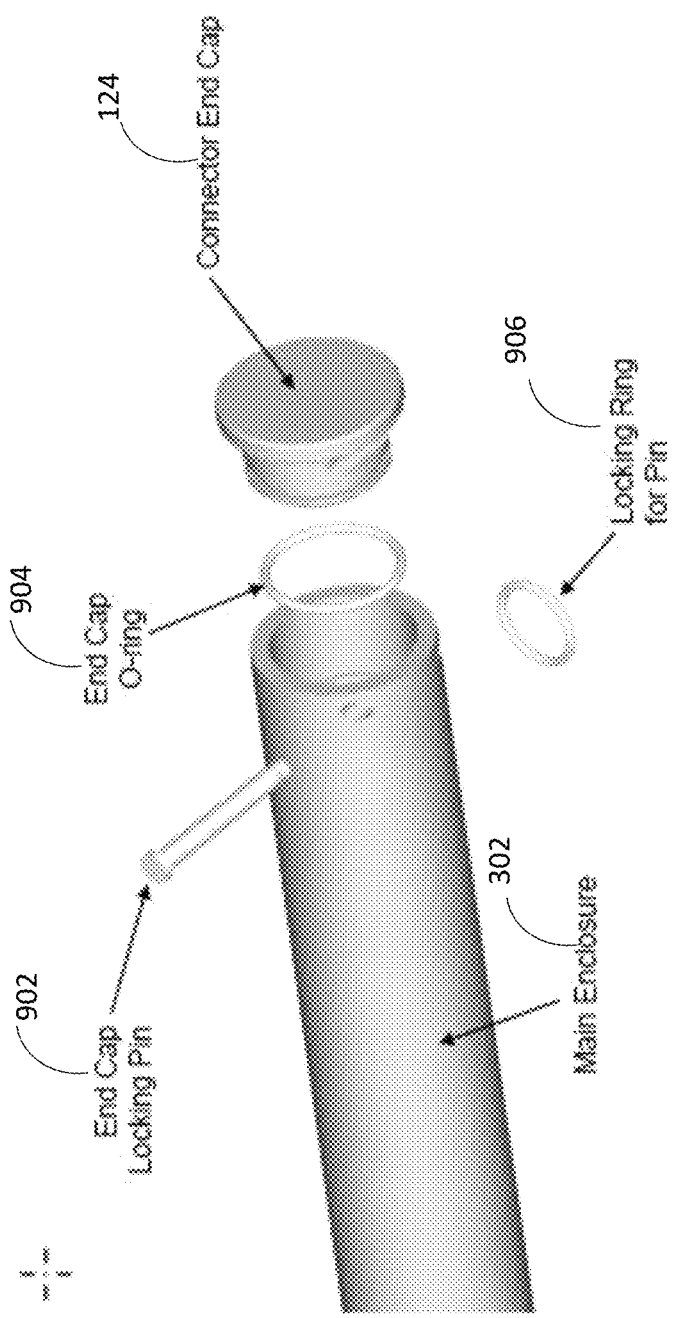
FIG. 9 is a diagram illustrating an exemplary end cap locking mechanism of a CCP system in accordance with an embodiment of the present disclosure.

FIG. 9 is a diagram illustrating an exemplary end cap locking mechanism of a CCP system in accordance with an embodiment of the present disclosure. In an embodiment, the end cap locking mechanism of FIG. 9 can be the same on both ends of a CCP system in accordance with an embodiment of the present disclosure. FIG. 9 shows an end cap locking pin 902, an end cap O-ring 904, and a locking ring for end cap locking pin 902.

Figure 10:
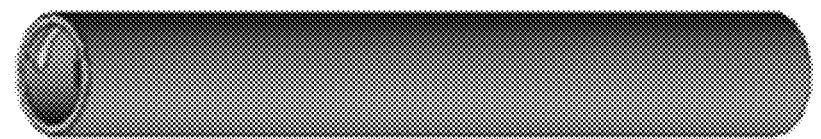
FIG. 10 is a diagram showing views of a main enclosure in accordance with an embodiment of the present disclosure.
Figure 10:
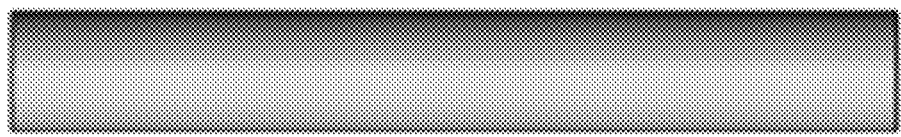
Figure 10:
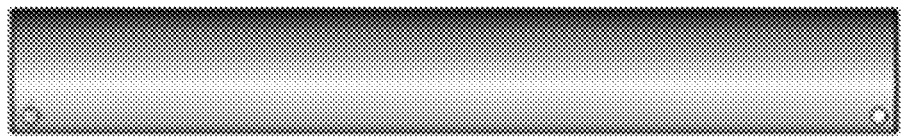

FIG. 10 is a diagram showing views of a main enclosure 302 in accordance with an embodiment of the present disclosure.

Figure 11:
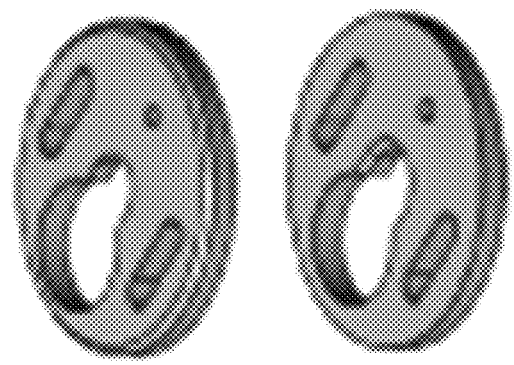
FIG. 11 is a diagram showing views of a probe locking ring in accordance with an embodiment of the present disclosure.

FIG. 11 is a diagram showing views of a probe locking ring 308 in accordance with an embodiment of the present disclosure.

Figure 12:
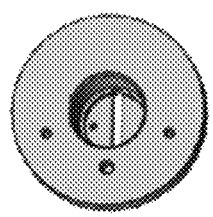
FIG. 12 is a diagram showing views of a probe end cap in accordance with an embodiment of the present disclosure.
Figure 12:
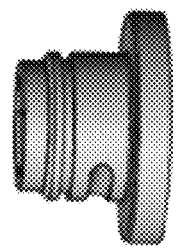

FIG. 12 is a diagram showing views of a probe end cap 106 in accordance with an embodiment of the present disclosure.

Figure 13:
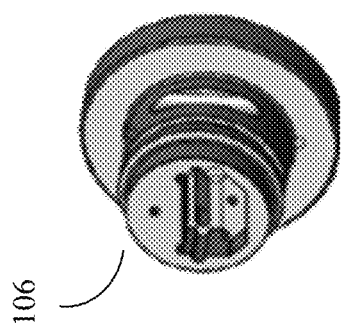
FIG. 13 is a diagram showing a probe end cap in accordance with an embodiment of the present disclosure.

FIG. 13 is a diagram showing a probe end cap 106 in accordance with an embodiment of the present disclosure.

Figure 14:
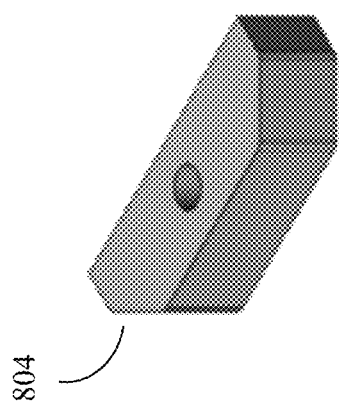
FIG. 14 is a diagram showing a probe lock bar in accordance with an embodiment of the present disclosure.

FIG. 14 is a diagram showing a probe lock bar 804806 in accordance with an embodiment of the present disclosure.

Figure 15:
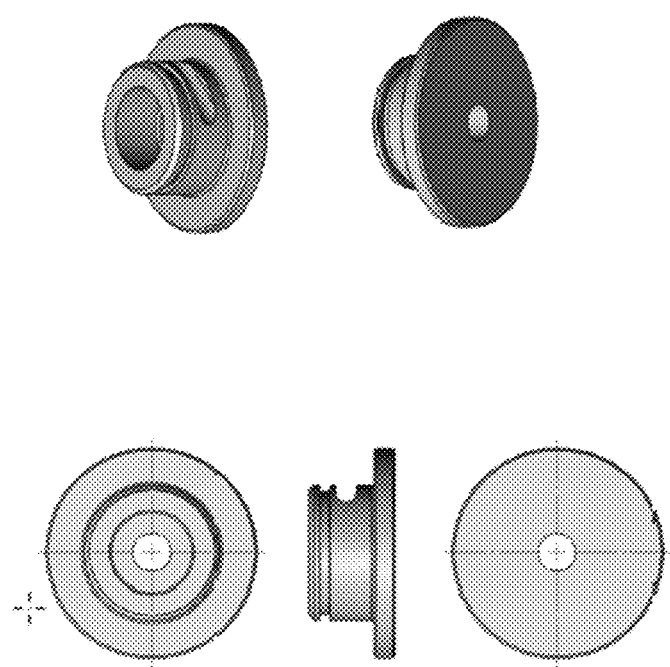
FIG. 15 is a diagram showing views of a connector endcap in accordance with an embodiment of the present disclosure.

FIG. 15 is a diagram showing views of a connector endcap in accordance with an embodiment of the present disclosure.

Figure 16:
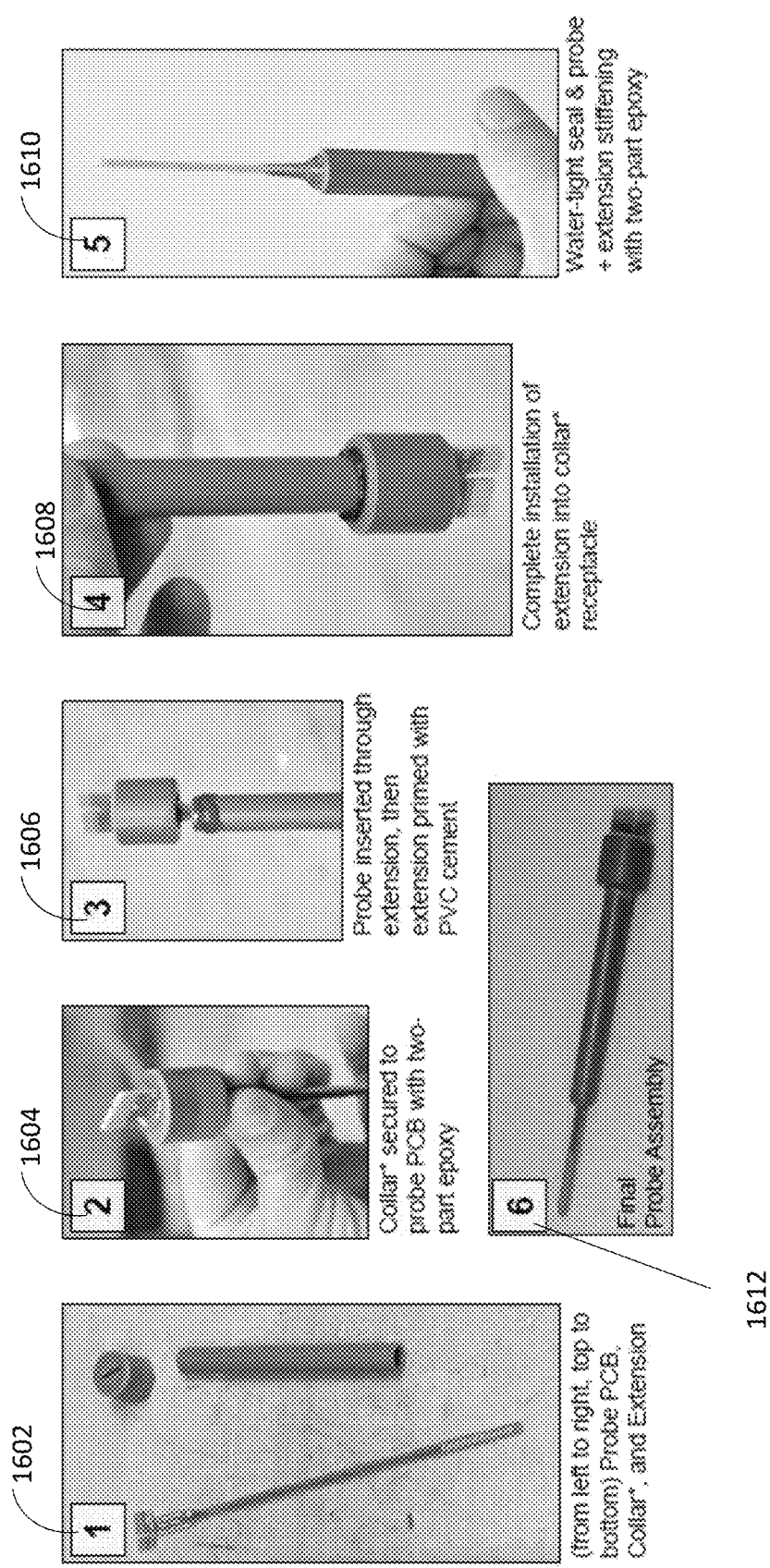
FIG. 16 shows images illustrating an exemplary probe assembly manufacturing procedure for an exemplary CCP system in accordance with an embodiment of the present disclosure.

FIG. 16 shows images illustrating an exemplary probe assembly manufacturing procedure for an exemplary CCP system in accordance with an embodiment of the present disclosure. In step 1602, probe 102, probe collar 310, and probe extension 104 are gathered. In step 1604, probe collar 310 is secured to probe 102 with two-part epoxy. In step 1606, probe 102 is inserted through probe extension 104, and probe extension 104 is primed with adhesive (e.g., PVC cement). In step 1608, the installation of probe extension 104 into the receptacle of probe collar 310 is completed. In step 1610, a water-tight seal is created, and probe 102 and probe extension 104 are stiffened with two-part epoxy. In step 1612, the final probe assembly is completed.

2.2. Integrated Electrical Systems of Exemplary CCP Systems

Figure 17:
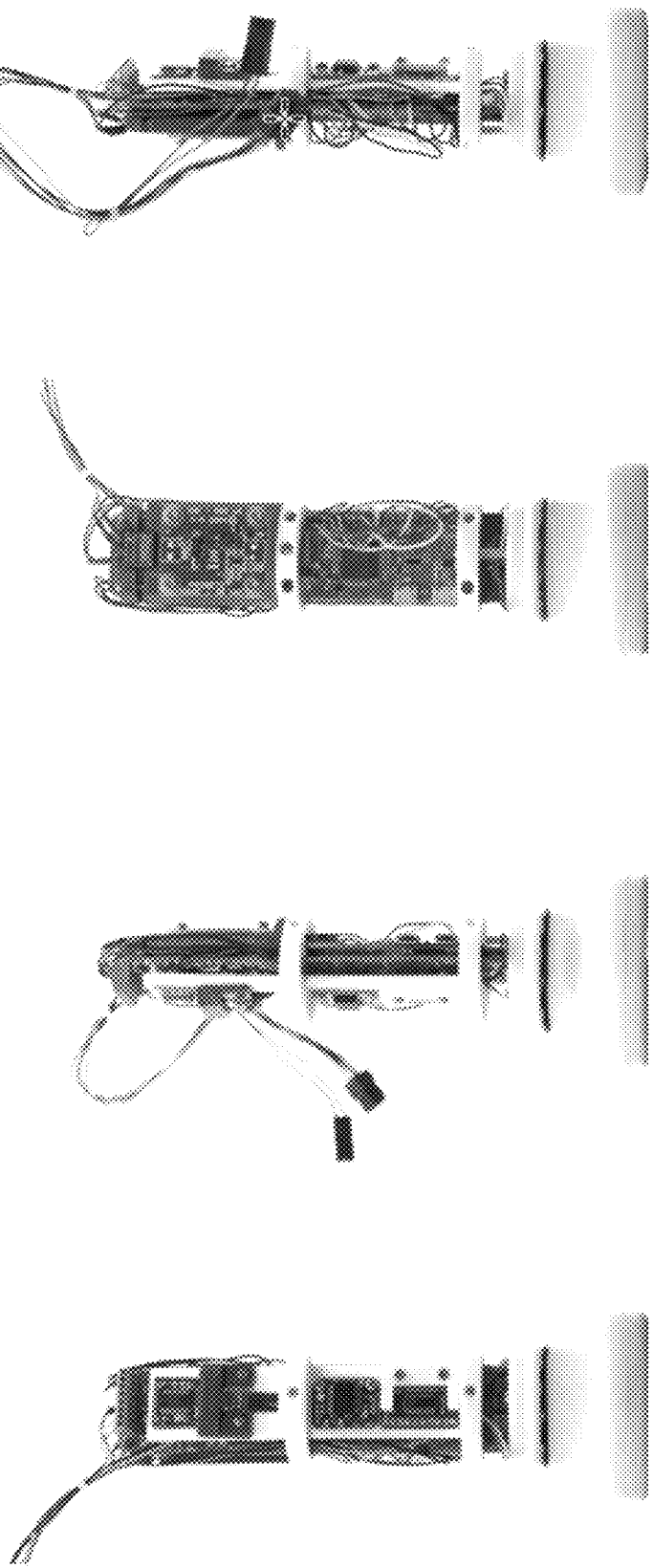
FIG. 17 shows images of an exemplary integrated electrical system for a CCP system in accordance with an embodiment of the present disclosure.

FIG. 17 shows images of an exemplary integrated electrical system for a CCP system in accordance with an embodiment of the present disclosure.

Figure 18:
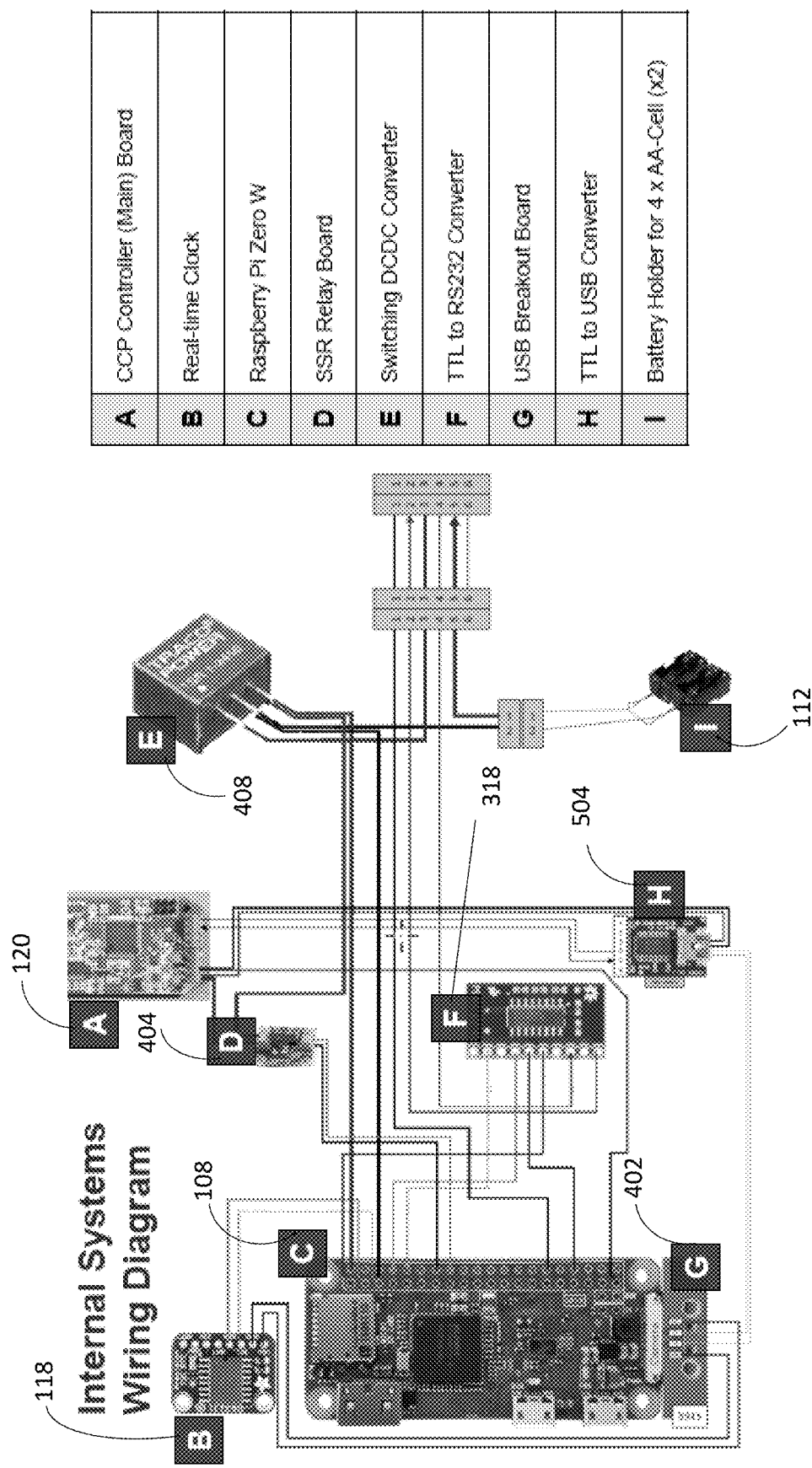
FIG. 18 shows an exemplary internal systems wiring diagram for a CCP system in accordance with an embodiment of the present disclosure.

FIG. 18 shows an exemplary internal systems wiring diagram for a CCP system in accordance with an embodiment of the present disclosure.

Figure 19:
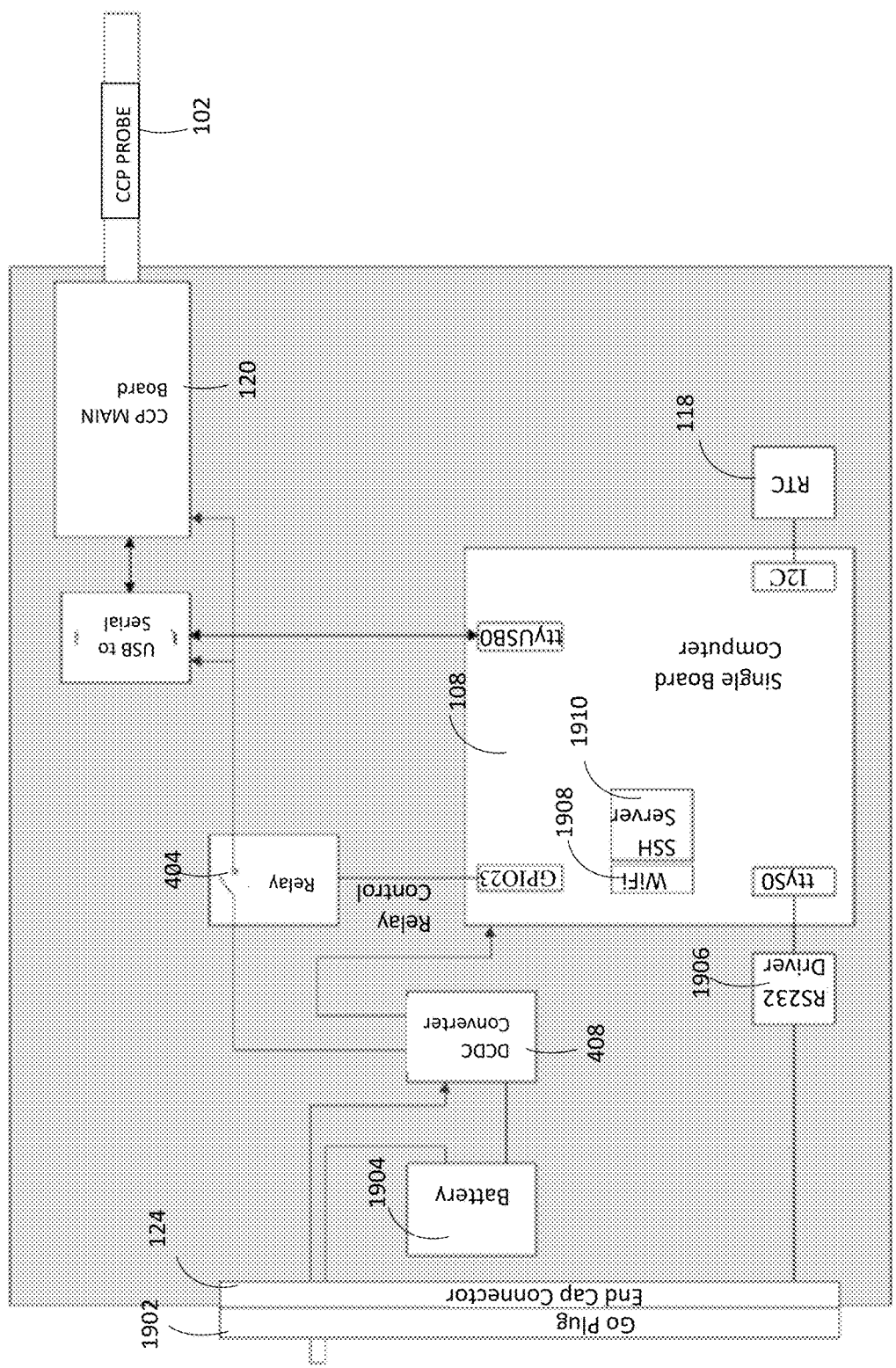
FIG. 19 shows a diagram of an exemplary hardware architecture for a CCP system in accordance with an embodiment of the present disclosure.

FIG. 19 shows a diagram of an exemplary hardware architecture for a CCP system in accordance with an embodiment of the present disclosure. FIG. 19 shows a go plug 1902, a battery 1904 (e.g., to fit into battery holder 112), and a RS232 driver 1906 (e.g., that fits into RS232 driver mounting tray 606). In FIG. 19, single board computer 108 includes a WiFi module 1908 and a secure shell (SSH) server 1910.

Figure 20:
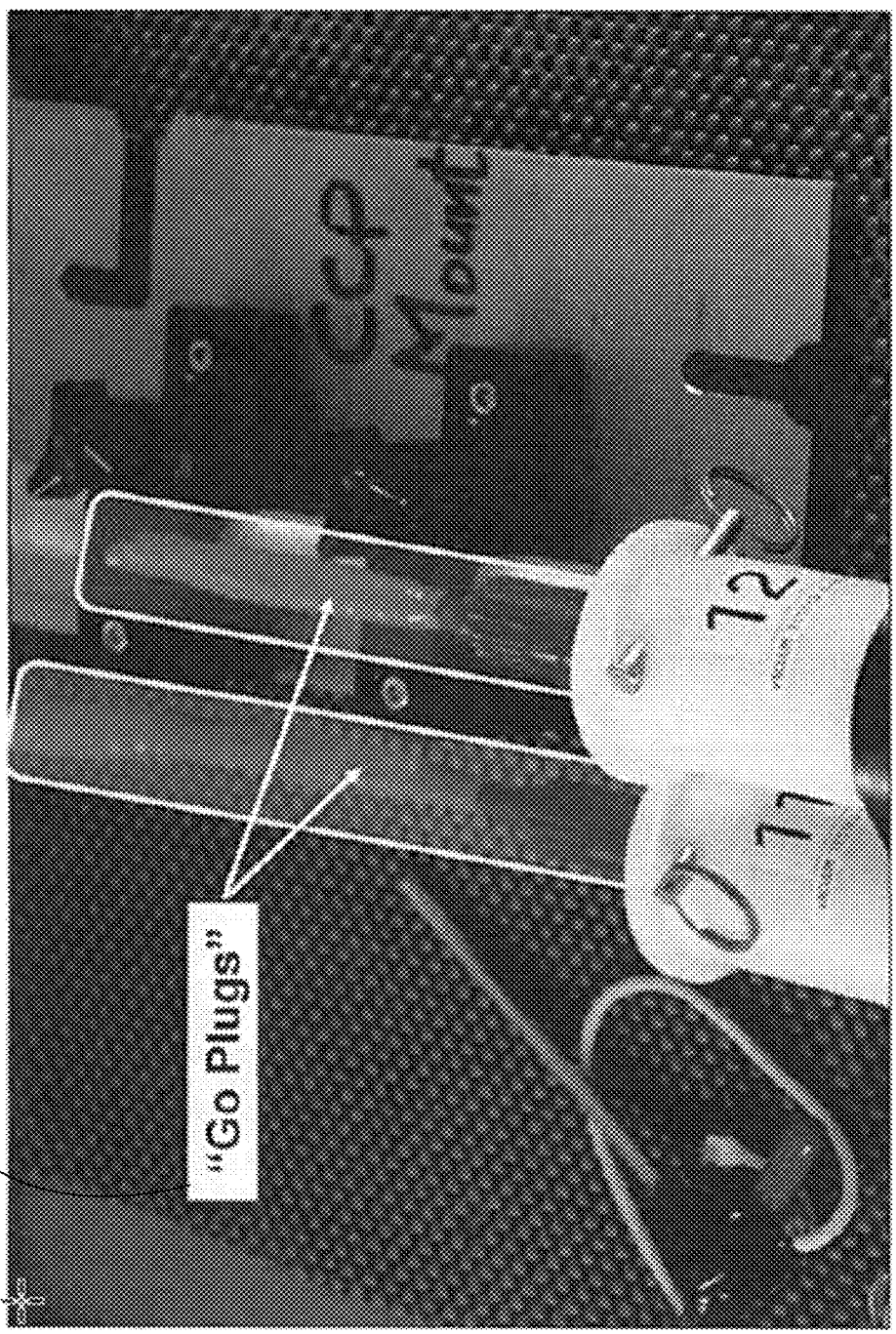
FIG. 20 shows images of exemplary go plugs for a CCP system in accordance with an embodiment of the present disclosure.

FIG. 20 shows images of exemplary go plugs for CCP systems in accordance with an embodiment of the present disclosure. In an embodiment, the go plugs are power shortening plugs that act as a power switch for a CCP system in accordance with an embodiment of the present disclosure. In an embodiment, when a go plug (or, in an embodiment, multiple go plus) is installed, the CCP system is on, and when a go plug is not installed, the CCP system is off. The go plugs can be used to enable self-logging in a CCP system in accordance with an embodiment of the present disclosure.

2.3. Rapid-Deployment Mechanisms of Exemplary CCP Systems

Figure 21:
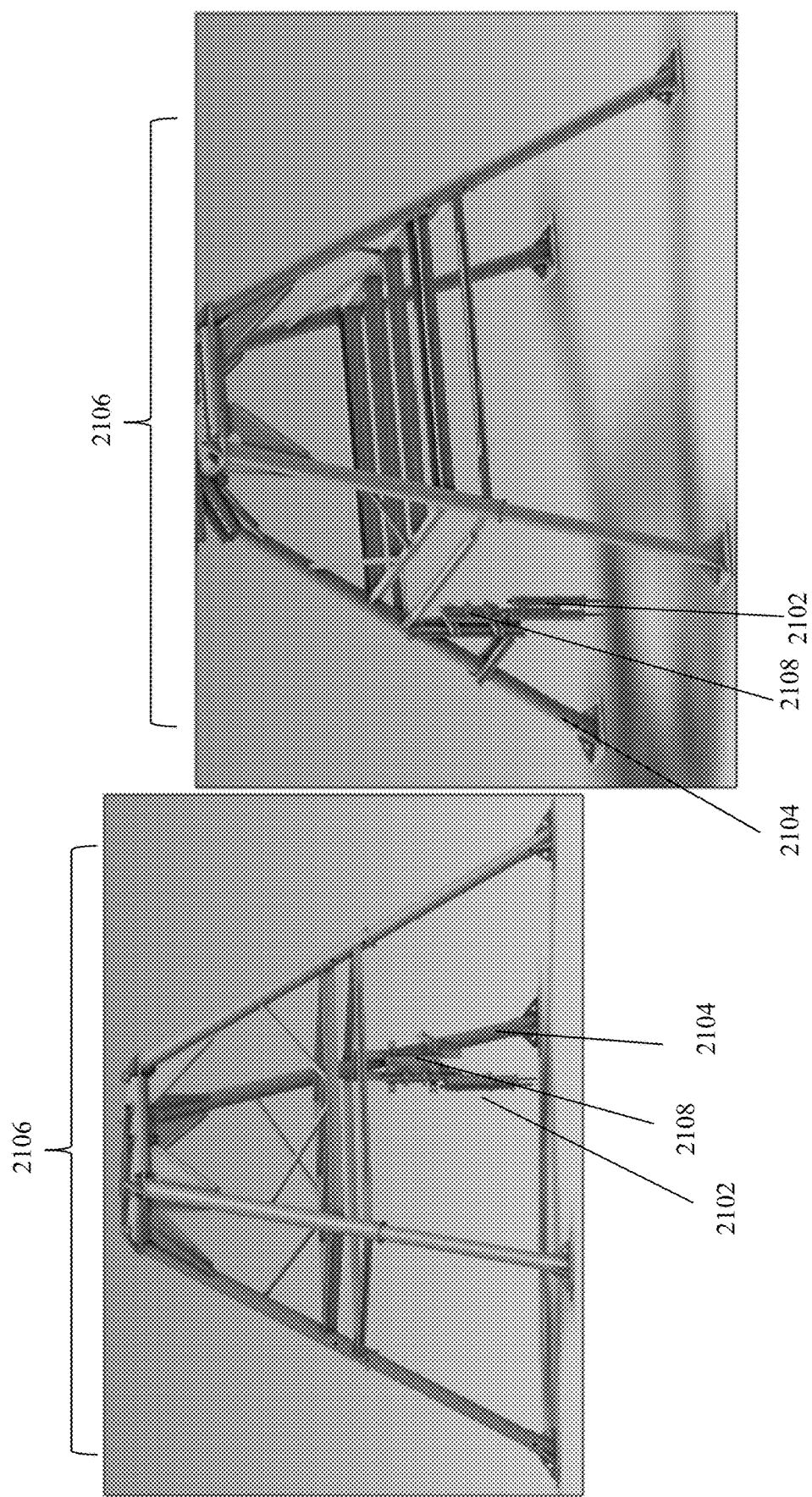
FIG. 21 shows images illustrating views of an exemplary rapid-deployment mechanism for a CCP system in accordance with an embodiment of the present disclosure.

FIG. 21 shows images illustrating views of an exemplary rapid-deployment mechanism 2106 for a CCP system 2102 in accordance with an embodiment of the present disclosure. As shown in FIG. 21, CCP system 2102 can be attached to a back plate 2108 affixed to a portion (e.g., a leg 2104) of the rapid-deployment mechanism 2106.

Figure 22:
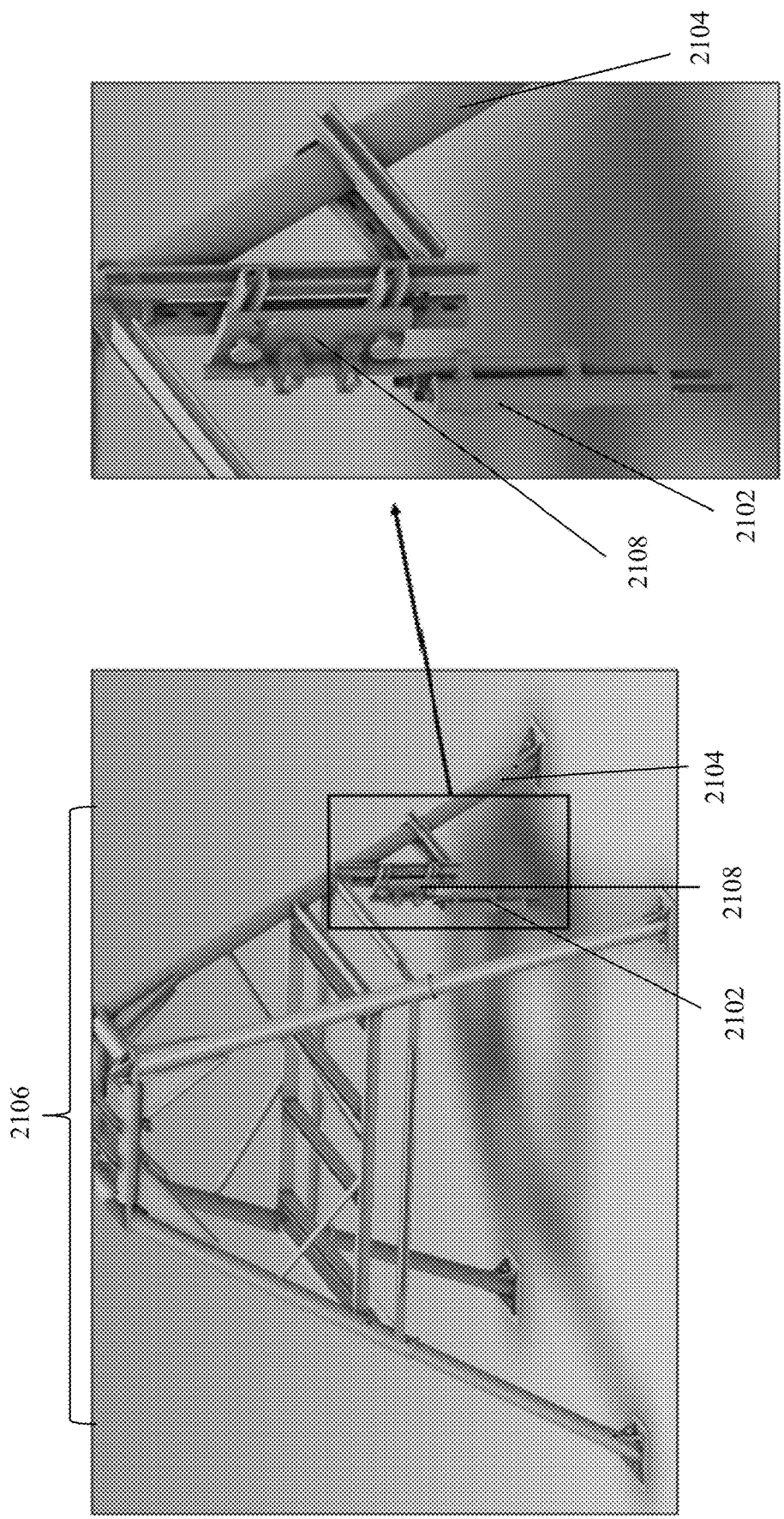
FIG. 22 shows additional images illustrating views of an exemplary rapid-deployment mechanism for a CCP system in accordance with an embodiment of the present disclosure.

FIG. 22 shows additional images illustrating views of an exemplary rapid-deployment mechanism for a CCP system in accordance with an embodiment of the present disclosure.

Figure 23:
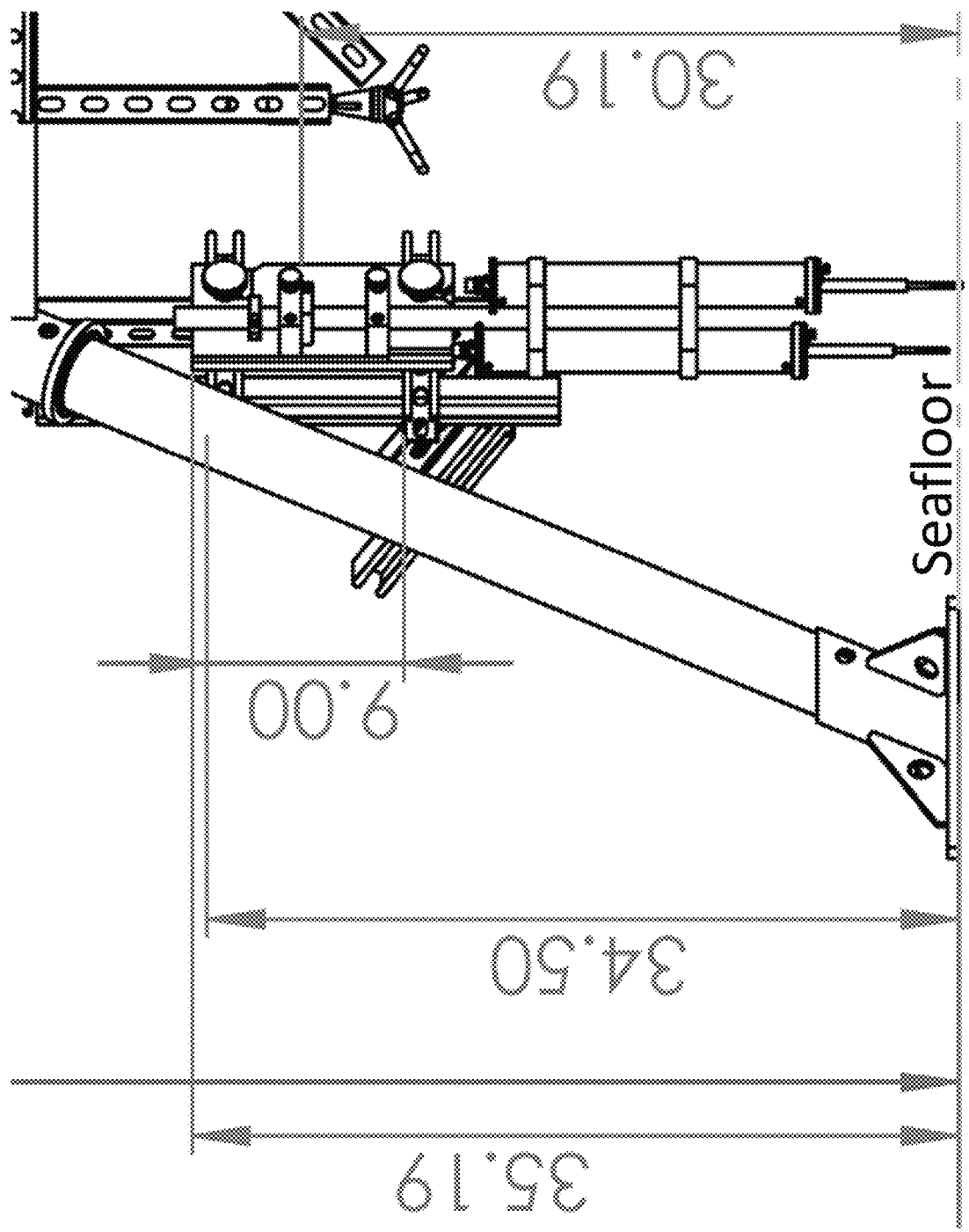
FIG. 23 is a diagram showing exemplary dimensions of an exemplary CCP system attached to a rapid-deployment mechanism operating on the seafloor in accordance with an embodiment of the present disclosure.

FIG. 23 is a diagram showing exemplary dimensions of an exemplary CCP system attached to a rapid-deployment mechanism operating on the seafloor in accordance with an embodiment of the present disclosure.

Figure 24:
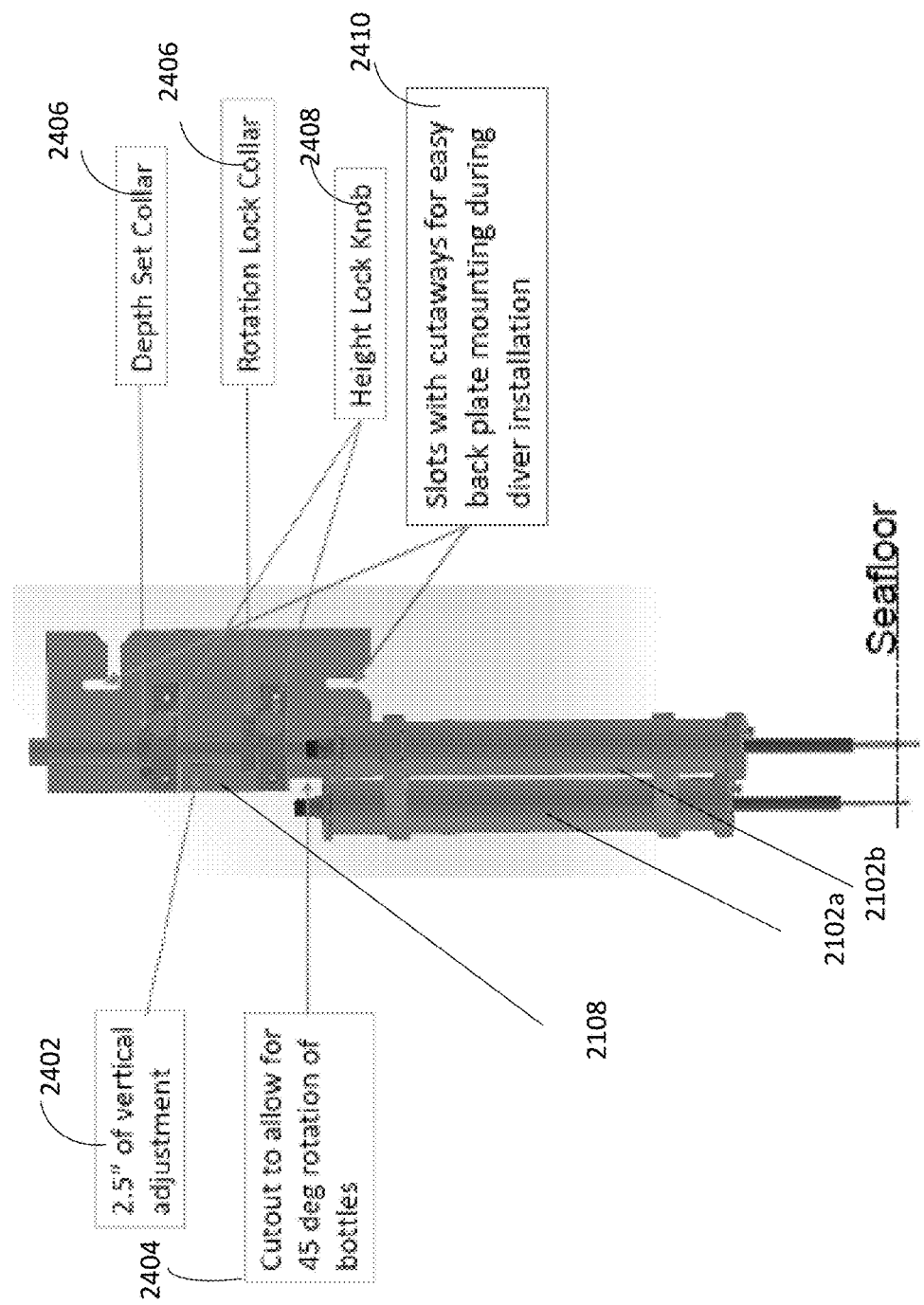
FIG. 24 is a diagram of an exemplary vertical adjustment mechanism of a CCP system in accordance with an embodiment of the present disclosure.

FIG. 24 is a diagram of an exemplary vertical adjustment mechanism of a CCP system in accordance with an embodiment of the present disclosure. In an embodiment, installation of the vertical adjustment mechanism (e.g., in an embodiment, allowing for 2.5 inches of vertical adjustment 2402) requires securing the lower slot around the knob on the pre-installed back plate first, then rotating the upper slit on the mounting plate over the knob on the pre-installed back plate. Then, in an embodiment, both back plate knobs can be tightened to secure the mounting assembly.

As shown in FIG. 24, multiple CCP systems (e.g., CCP systems 2102a and 2102b) can be attached to a single rapid-deployment mechanism 2106. For example, in an embodiment, with a paired assembly deployment (e.g., two CCP systems 2102a and 2102b deployed together), with zero offset, embodiments of the present disclosure enable doubling of continuous data collection time (from 20 hours to 40 hours) by staggering the deployment start times. FIG. 24 also shows a cutout to allow 45 degrees of rotation for CCP systems 2102a and 2102b, a depth set collar 2406, a rotation lock collar 2406, a height lock knob 2408, and slots 2410 with cutaways for easy back plate mounting during diver installation.

Figure 25:
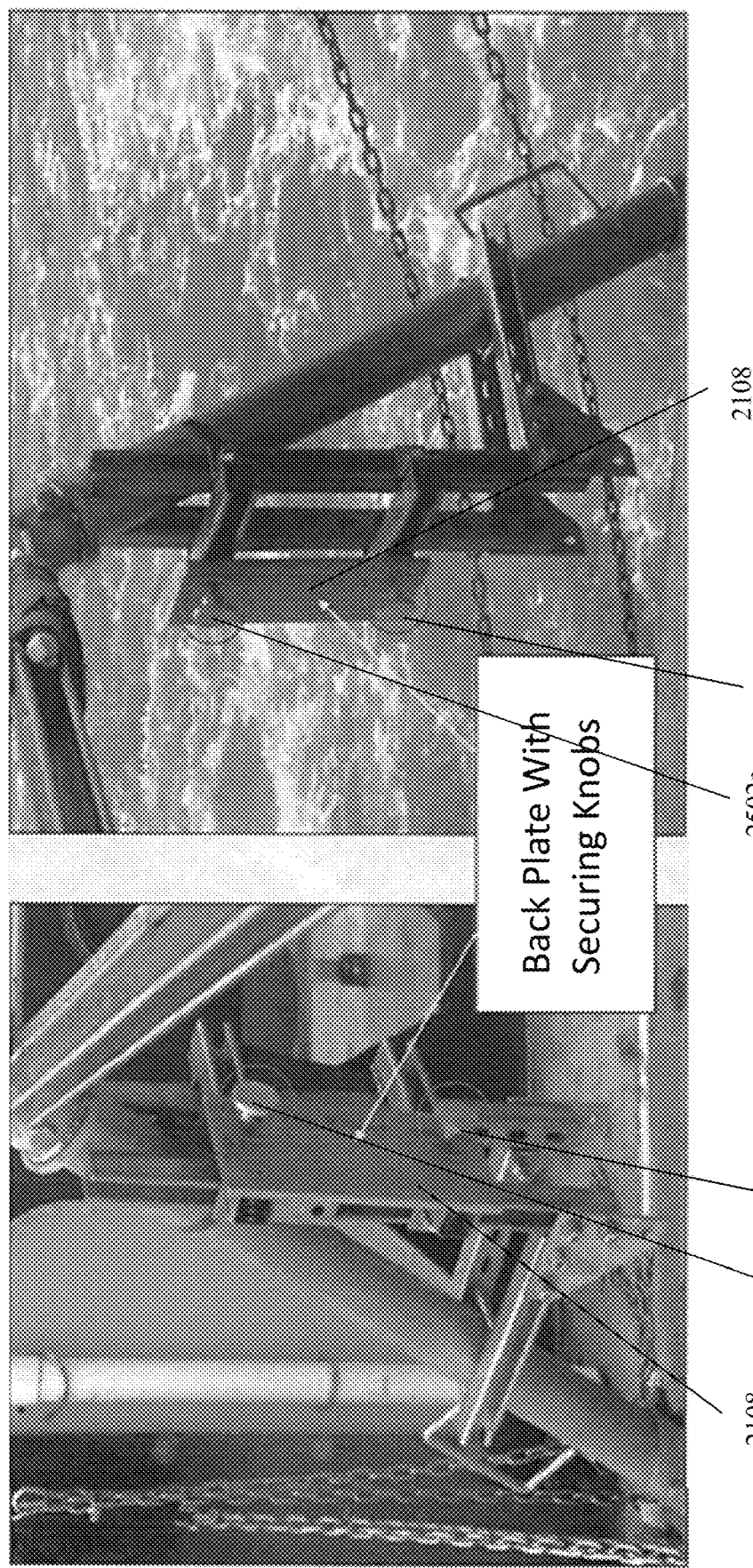
FIG. 25 shows images of an exemplary back plate of a rapid deployment mechanism with mounting plate securing knobs for mounting an exemplary CCP system in accordance with an embodiment of the present disclosure.

FIG. 25 shows images of an exemplary back plate 2108 of a rapid deployment mechanism with mounting plate securing knobs 2502a and 2502b for mounting an exemplary CCP system 2102 in accordance with an embodiment of the present disclosure. In an embodiment, mounting plate securing knobs 2502 and 2502b are large knurled securing knobs to enable ease of use by a diver.

Figure 26:
FIG. 26 shows an image from an exemplary field experiment equipment recovery cruise in accordance with an embodiment of the present disclosure.

FIG. 26 shows an image from an exemplary field experiment equipment recovery cruise in accordance with an embodiment of the present disclosure. In an embodiment, a CCP system in accordance with an embodiment of the present disclosure can be handed off to a diver, who can detach a prior CCP system mounted to a rapid-deployment mechanism operating on the seafloor (e.g., to collect data for analysis) and reattach a replacement CCP system to the rapid-deployment mechanism (e.g., to continue gathering data).

Figure 27:
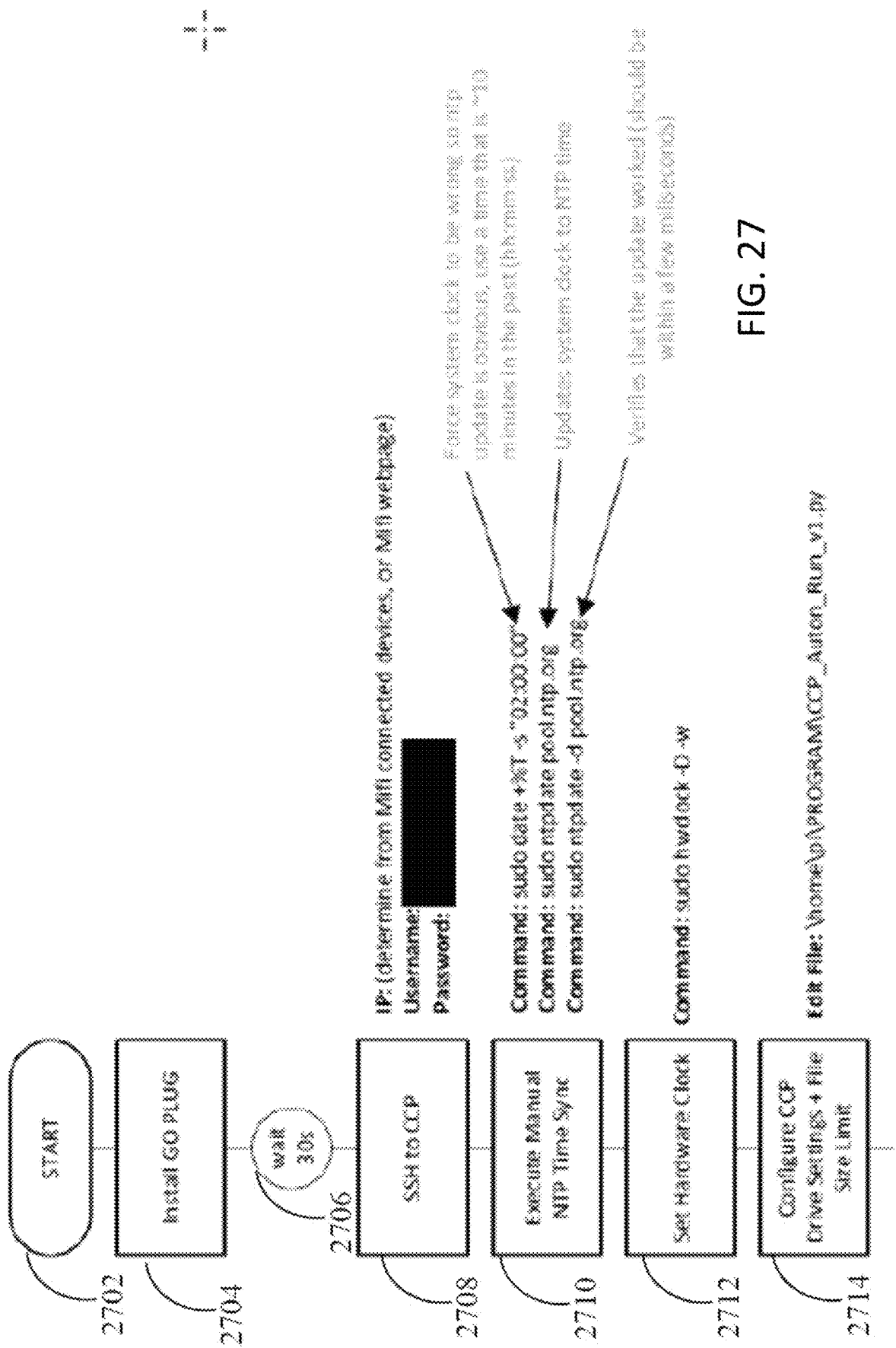
FIG. 27 is a flowchart of an exemplary method for deploying a CCP system in accordance with an embodiment of the present disclosure.
Figure 27:
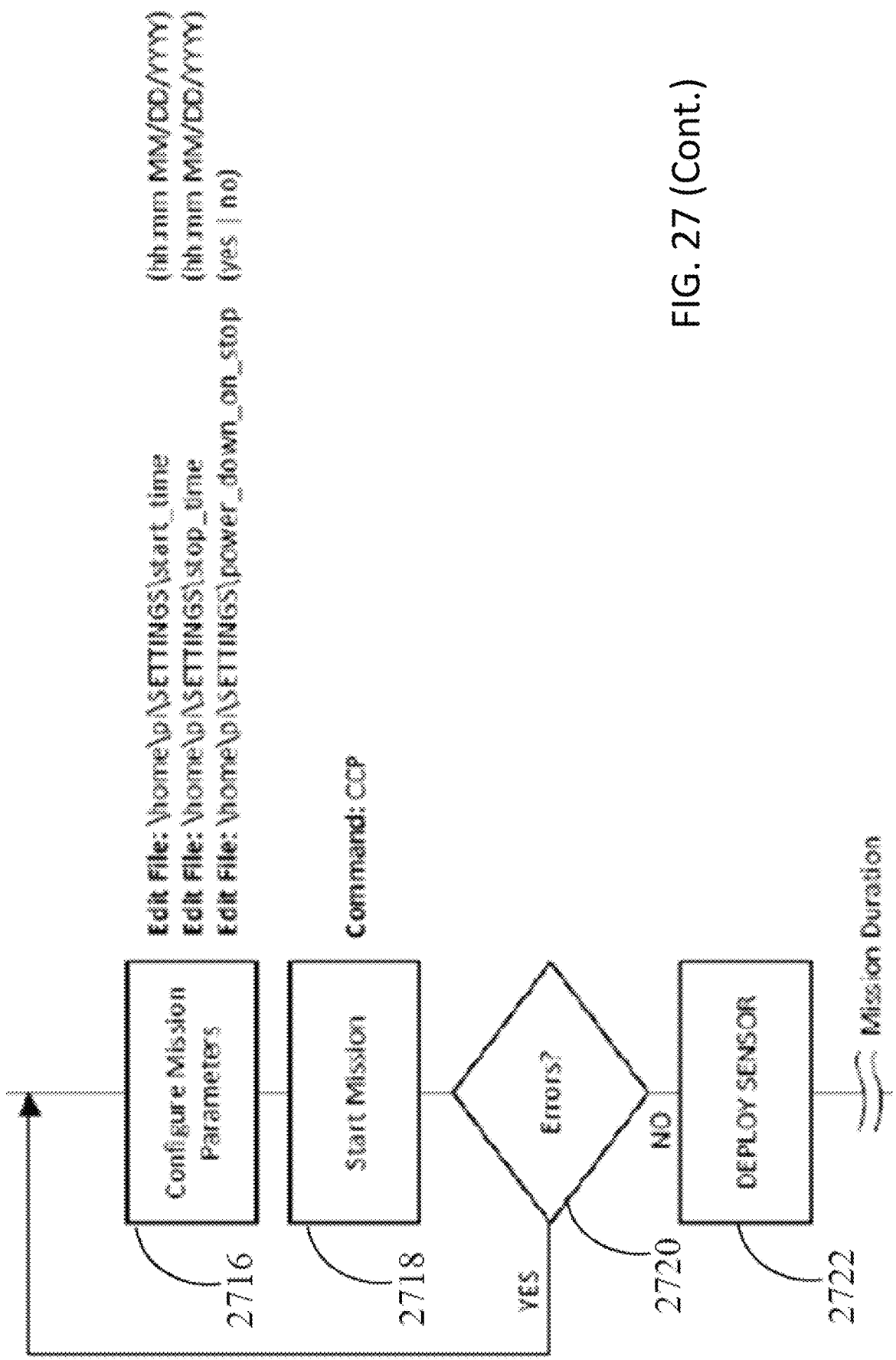

FIG. 27 is a flowchart of an exemplary method for deploying a CCP system in accordance with an embodiment of the present disclosure. In FIG. 27, the method starts 2702 at step 2704, wherein a go plug 1902 is installed into a CCP system 2102, which enables power to single board computer 108. In step 2706, there is a wait in an embodiment (e.g., a 30s wait) during boot up of CCP system 2102. In step 2708, an SSH connection is established with the CCP system 2102 for a mission controller to configure settings (e.g., mission parameters). In step 2710, a manual Network Time Protocol (NTP) time sync is executed. In step 2712, the hardware clock of the CCP system 2102 is set. In step 2714, the drive settings and file size limit of the CCP system 2102 is configured. In step 2716, the mission parameters of the CCP system 2102 are configured. In step 2718, the mission is started. In step 2720, error messages are presented to the mission controller, if detected, and if so, the method returns to step 2716 for the mission controller to resolve the errors. In step 2722, a sensor (e.g., in an embodiment, CCP system 2102) is deployed.

Figure 28:
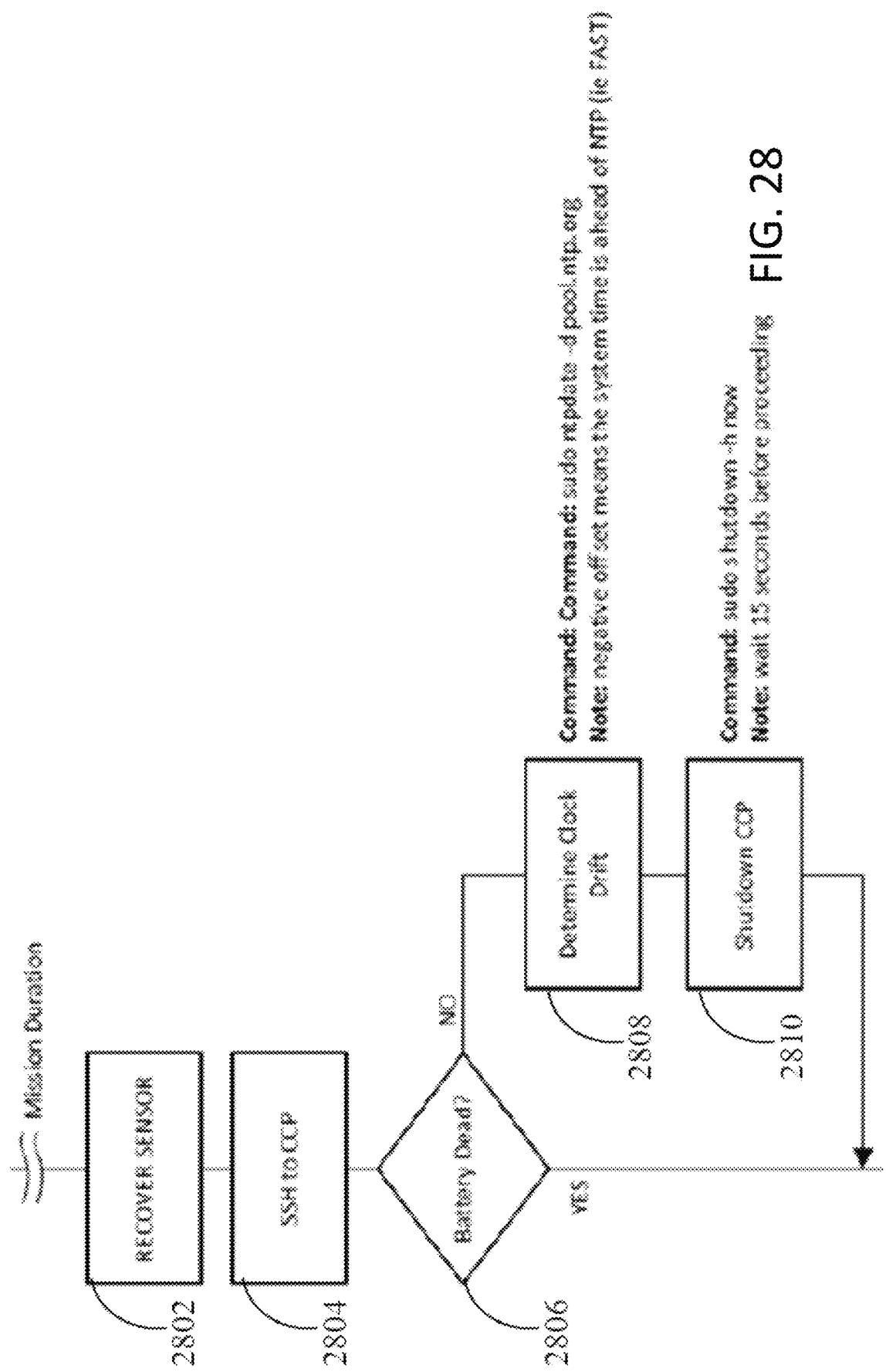
FIG. 28 is a flowchart of an exemplary method for recovering a CCP system in accordance with an embodiment of the present disclosure.
Figure 28:
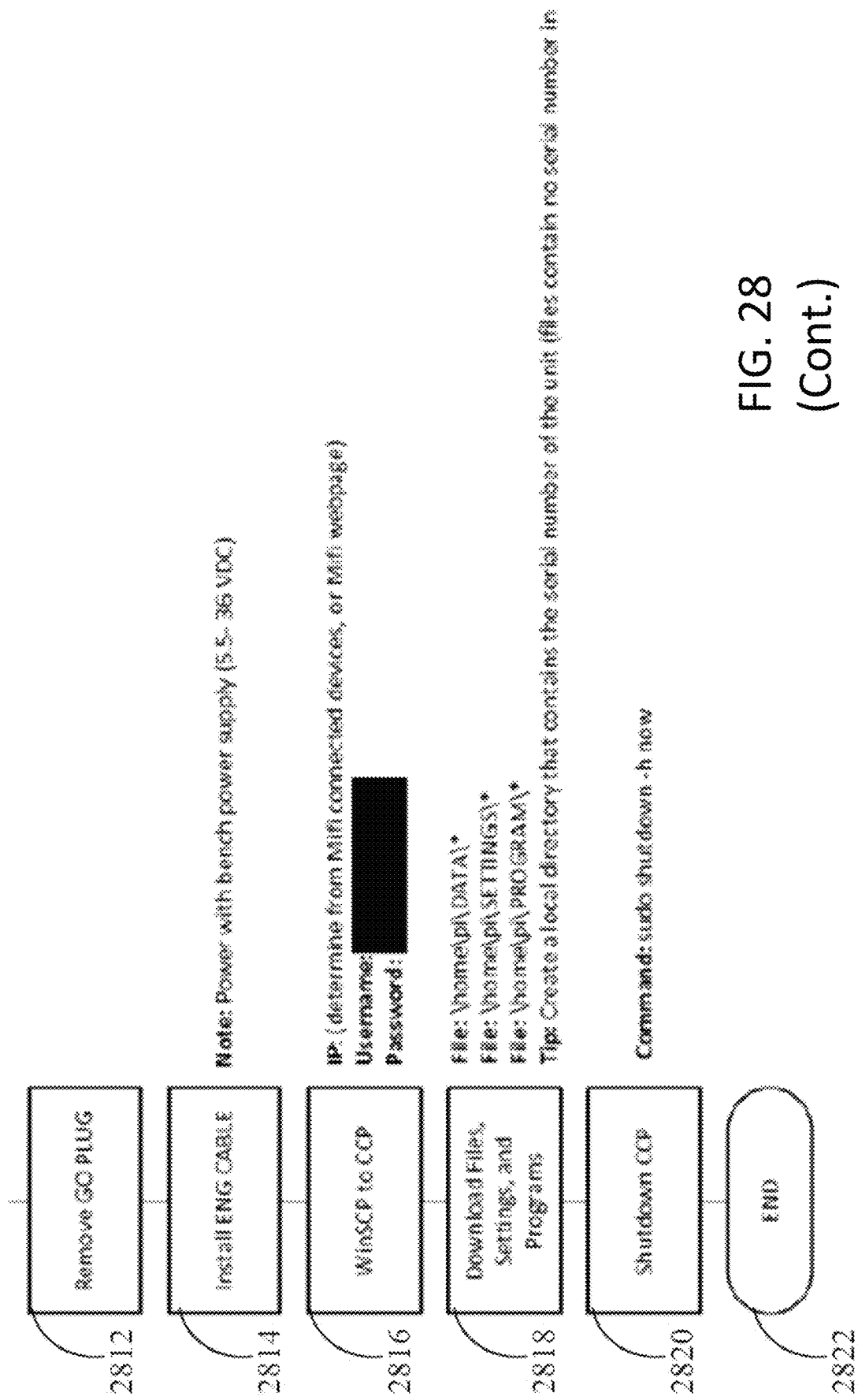

FIG. 28 is a flowchart of an exemplary method for recovering a CCP system in accordance with an embodiment of the present disclosure. In an embodiment, the method of FIG. 28 begins where the method of FIG. 27 ends. In step 2802, the sensor is recovered (e.g., in an embodiment, a diver recovers CCP system 2102). In step 2804, the mission controller establishes an SSH connection with CCP system 2102. In step 2806, a determination is made regarding whether battery 1904 is dead. If battery 1904 is dead, the method proceeds to step 2812. If battery 1904 is not dead, the method proceeds to step 2808. In step 2808, the clock drift is determined. In step 2810, CCP system 2102 is shut down. In step 2812, go plug 1902 is removed from CCP system 2102. In step 2814, an engineering cable is installed. In step 2816, a Secure Copy, SCP (e.g., Windows Secure Copy, WinSCP) message is sent to CCP system 2102. In step 2818, files, settings, and programs are downloaded from CCP system 2102. In step 2820, CCP system 2102 is shut down and the method ends 2822.

In an embodiment, when a CCP system in accordance with an embodiment of the present disclosure was installed on the seafloor in roughly 16 meters of water depth, the systems operated for roughly 20 hours each before the electrode plating on the probes corroded beyond the threshold for accurate sampling, due to electrolysis.

2.4. Autonomous Data Logging of Exemplary CCP Systems

In an embodiment, once the CCP system has been installed (e.g., by attaching it to a rapid-deployment mechanism and lowering the rapid-deployment mechanism to the seafloor or via a diver attaching the CCP system to an installation already on the seafloor), the CCP system can be instructed to start a mission (e.g., in an embodiment, begin collecting data). In an embodiment, this can be done via a command (e.g., via a signal sent to the CCP system, such as to a controller installed on the PCB of the CCP system) or a switch (e.g., a switch on the CCP system coupled to a controller on the PCB). In an embodiment, the CCP system can be instructed to begin the mission via the installation of a go plug (e.g., prior to deployment).

In an embodiment, mission parameters can be configured into the CCP. For example, in an embodiment, a signal can be sent to the controller of the PCB system of the CCP system informing the controller of the mission parameters. In an embodiment, these mission parameters can be sent to the controller before the CCP system is attached to a rapid-deployment mechanism so that the CCP system can start the mission according to the mission parameters when the CCP system is instructed to start the mission. In an embodiment, these mission parameters can be sent to the controller over a wireless communication link (e.g., SSH) prior to the CCP system deployment. For example, in an embodiment, the mission parameters can be programmed by a user to instruct the CCP system to sample with a specific set of voltage drive strength parameters, specific start times, or specific sample rates and/or durations. In an embodiment, the go plug starts the CCP system, and it wakes up and reads the mission parameters. In an embodiment, if the CCP system is not scheduled to start right away (e.g., based on the mission parameters), it goes into low-power mode to conserve power (e.g., until the mission parameters instruct the CCP system to wake up and begin its scheduled tasks).

In an embodiment, a sensor attached to the CCP system or to the rapid-deployment mechanism can be used with software integration to identify corrosion of the probes of the CCP system and can send this information to the CCP system (e.g., to the single board computer of the CCP system). In an embodiment, the mission parameters can instruct the CCP system to continue gathering data until a threshold amount of corrosion has occurred on the probes of the CCP system. In an embodiment, once this threshold is reached, the CCP system can send a signal (e.g., a wireless signal) notifying another CCP system to begin sampling (e.g., since the corrosion threshold has been reached on the currently active CCP system). By deploying multiple CCP systems, wherein one (or some) CCP systems are in low power mode and one (or some) are active, power can be conserved, and mission duration can be increased.

In an embodiment, mission parameters for the CCP system can be stored in a file (e.g., in an embodiment, a plain text file) containing mission settings. In an embodiment, a logfile (e.g., in an embodiment, a plain text file) can contain all CCP transactions with timestamps. In an embodiment, code, such as Python code or bash scripts, can schedule the recording of data. In an embodiment, the CCP system can generate files based on the data recorded by the CCP system. In an embodiment, the mission parameters (and/or bash scripts) can instruct the CCP system to use staggered start times for data collection to conserve power of the CCP system.

3. Exemplary Advantages

CCP systems in accordance with an embodiments of the present disclosure have improved mechanical designs, provide integrated electrical systems, have a rapid-deployment mechanism, and enable autonomous data logging. CCP systems in accordance with embodiments of the present disclosure avoid the need for cables and multiple external bottles (e.g., for batteries, logging systems) that would become prohibitive for diver deployment and retrieval, for any coastal/ocean deployment/retrieval away from the coastline, during a storm event, in a remote area, etc. A self-contained, miniature, lightweight system in accordance with an embodiment of the present disclosure enables the use of an excellent mounting/deployment system.

Embodiments of the present disclosure further provide a system for rapid- and easy-deployment, especially by divers in low- to zero-visibility conditions. A rapid-deployment system in accordance with an embodiment of the present disclosure is flexible and able to be adapted to changing environments and is capable of keeping track of measurement bin vertical locations.

A probe end cap and PCB mounting mechanism in accordance with an embodiment of the present disclosure enables more secure mounting and reduces the quantity of poor data quality due to loose or cross-pin connections. Further, in an embodiment, the end cap reduces the water intrusion risk, increasing the range of deployment conditions (e.g., deeper water, large wave storm conditions, etc.)

In an embodiment, an exemplary CCP system includes a probe collar that converts the thin PCB profile into a durable, cylindrical shape. In an embodiment, the probe collar enables a water-tight seal through the use of O-rings, and a narrow slit ensures proper probe orientation. Further, in an embodiment, an exemplary PCB system includes a receptacle for a probe collar extension. In an embodiment, a probe collar extension provides enhanced stiffness and durability for the PCB system. In an embodiment, the probe extension enables an easy installation, allows for deployment in energetic flows, enables easy, watertight installation through the underside of flow tunnels or wave flumes due to its cylindrical shape, and has a small profile, enabling minimal flow interference and maximum stiffness.

In an embodiment, an exemplary CCP system includes a probe endcap design that has several advantages over prior systems. For example, in an embodiment, the probe endcap design enables deeper deployment depths, is more reliable against water intrusion, enables fewer leaks, and enables sturdier mating with the PCI express edge card connector, resulting in better data quality. Further, in an embodiment, the probe endcap design enables easy-to-swap probes, which may be necessary for when a probe accidentally breaks during deployment or to replace the probe after 20+ hours of continuous use.

In an embodiment, an exemplary CCP system includes a mounting and deployment mechanism (e.g., a rapid-deployment mechanism) for a standalone CCP assembly that can be rotated to align the thin face of probes with varying flow directions. In an embodiment, a dual rod level indicator design enables lowering of CCP assemblies into the sand after installation (which is the stage where the ambiguity of measurement bin elevation is introduced), even in low-to-zero visibility, preserving the fragile probes and bed state. In an embodiment, at the same time, millimeter-level vertical accuracy for the elevation of each measurement bin is maintained after retrieval, when the assembly is raised to protect the fragile probes (e.g., if the bed has accreted, thus, burying more of the probes). The fast-capable deployment enabled by embodiments of the preset disclosure enhances rapid-response storm event deployment and/or adjustment capability, where time is usually in short supply.

Embodiments of the preset disclosure provide flexibility to adapt to large-scale bed changes by giving the user the ability to raise/lower the assembly installment height on the mounting rod. Embodiments of the preset disclosure provide systems that are easily and quickly installed/retrieved by divers, even in low- to zero-visibility conditions, which allows for more bottom time to complete other tasks for ocean observation systems. Embodiments of the preset disclosure include minimal mechanical moving parts using a design that reduces failure modes.

In an embodiment, the CCP system can be powered on and off without opening the pressure vessel, which mitigates against leaks and flooding of the pressure vessel. In an embodiment, one or more go plugs are used to power the CCP system on and off without opening the pressure vessel.

Embodiments of the present disclosure enable longer deployment duration (e.g., using staggered start times) and larger vertical range (enabling the CCP system to be deployed in more dynamic environments, with less down time for adjustments). In an embodiment, the CCP system can be deployed with 100% overlap (i.e., no offset), which gives spatially separated observations (e.g., velocity of the sediment in the sheet flow layer).

In an embodiment, a CCP system enables program system settings via remote control of the CCP system (e.g., via virtual desktop or SSH) and requires no communications (serial) cable connection for system configuration and/or data collection. In an embodiment, a CCP system requires no power cable if internal batteries are installed, enables internal, autonomous data logging (no topside computer required). In an embodiment, a CCP system is burst mode capable (e.g., instead of using continuous sampling), which increases probe life by prolonging onset of electrolysis-induced corrosion. For example, in an embodiment, a PCB system can be instructed (e.g., via mission control settings) to delay the start of logging, while minimizing battery drain in low power mode. In an embodiment, this can be supported via a hardware incorporated switch in internal system electronics architecture, activated and de-activated via a shell script. In an embodiment, with a paired assembly deployment (e.g., two CCP systems deployed together), with zero offset, embodiments of the present disclosure enable doubling of continuous data collection time (from 20 hours to 40 hours) by staggering the deployment start times.

Embodiments of the present disclosure can be used to measure scour development and evolution around infrastructure (e.g., during a tsunami), bridge and pier piles, coastal structures, (e.g., jetties), and unexploded ordnance/mine burial. Embodiments of the present disclosure can be used to measure fundamental sediment transport processes, instantaneous bed levels (e.g., dune overwash, morphology during storms, intra-swash/infragravity scales and momentary bed failures, etc.), and ripple formation and migration.

4. Conclusion

It is to be appreciated that the Detailed Description, and not the Abstract, is intended to be used to interpret the claims. The Abstract may set forth one or more but not all exemplary embodiments of the present disclosure as contemplated by the inventor(s), and thus, is not intended to limit the present disclosure and the appended claims in any way.

The present disclosure has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

While various embodiments of the present disclosure have been described above, it should be understood that they have been presented by way of example only, and not limitation. It will be apparent to persons skilled in the relevant art that various changes in form and detail can be made therein without departing from the spirit and scope of the disclosure. Thus, the breadth and scope of the present disclosure should not be limited by any of the above-described exemplary embodiments.

What is claimed is:

1. A system for conductivity concentration profiling, the system comprising:
a deployment mechanism configured to be lowered to a seafloor, wherein the lowered deployment mechanism contacts the seafloor; and
a conductivity concentration profiler (CCP) system coupled to the deployment mechanism, wherein the CCP system is configured to be detachable from the deployment mechanism, wherein the CCP system, once detached from the deployment mechanism, is not coupled to any other object, and wherein the CCP system comprises a probe located at a distal end of the CCP system, the probe being configured to measure sediment concentration in water around the deployment mechanism, wherein the CCP system comprises an adjustment mechanism allowing for vertical adjustment of the CCP system relative to the lowered deployment mechanism allowing a tip of the probe to maintain contact with the seafloor when deployed,
wherein the CCP system further comprises:
an enclosure coupled to the probe, wherein the enclosure comprises:
a probe side endcap coupled to the probe;
a printed circuit board (PCB) coupled to the probe side endcap, wherein the PCB comprises a controller configured to receive data regarding the sediment concentration from the probe and transmit the data for storage; and
a battery coupled to the PCB;
wherein the controller, independent of a cable connection external to the CCP system, controls the CCP system in a burst sampling mode to activate and to de-activate an active logging of measured data when the CCP system is deployed to minimize battery drain.

2. The system of claim 1, wherein the deployment mechanism further comprises a back plate, and wherein the CCP system is configured to be coupled to the back plate via knurled securing knobs.

3. The system of claim 2, wherein the back plate is coupled to a leg of the deployment mechanism.

4. The CCP system of claim 2, wherein the enclosure further comprises:
a connector side endcap coupled to an end of the enclosure opposite the probe side endcap; and
a go plug coupled to the connector side endcap and to the battery, wherein the go plug is configured to power the battery without opening the enclosure.

5. The CCP system of claim 4, further comprising:
a direct current (DC) to DC converter coupled to the go plug, to the PCB, and to the battery.

6. The CCP system of claim 1, further comprising:
a second CCP system coupled to the deployment mechanism.

7. The system of claim 1, wherein the controller, independent of a cable connection external to the CPP system, controls the CCP system in the burst sampling mode to activate and to de-activate the active logging of measured data via an internal switch that is activated and de-activated via a shell script.

* * * * *